United States Patent [19]

Dubroeucq et al.

[11] Patent Number: 5,112,988
[45] Date of Patent: May 12, 1992

[54] ISOINDOLONE DERIVATIVES

[75] Inventors: Marie-Christine Dubroeucq, Enghien les Bains; Claude Moutonnier, le Plessis Robinson; Jean-Francois Peyronel, Palaiseau; Michel Tabart, Paris; Alain Truchon, Lyon, all of France

[73] Assignee: Rhone-Poulenc Sante, France

[21] Appl. No.: 616,044

[22] Filed: Nov. 20, 1990

[30] Foreign Application Priority Data

Nov. 23, 1989 [FR] France ................... 89 15407

[51] Int. Cl.$^5$ .......................... C07D 209/44
[52] U.S. Cl. ................................ 548/470
[58] Field of Search ......................... 548/470

[56] References Cited

U.S. PATENT DOCUMENTS 4,494,547  1/1985  Myers ................. 548/470

Primary Examiner—Mary C. Lee
Assistant Examiner—Joseph K. McKane
Attorney, Agent, or Firm—Morgan & Finnegan

[57] ABSTRACT

New isoindolone derivatives of general formula (I) are

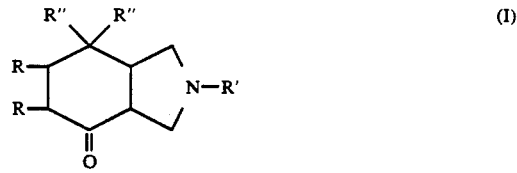

disclosed in which the radicals R represent hydrogen atoms or, together, form a bond, the symbol R' represents a hydrogen atom or a readily removable radical and the symbols R" are identical and represent phenyl radicals which can be substituted with a halogen atom or a methyl radical at the ortho or meta position, in the (3aR, 7aR) form or in the form of a mixture of the (3aRS, 7aRS) forms, as well as their salts.

These derivatives are useful as intermediates for the preparation of therapeutically active products.

8 Claims, No Drawings

ISOINDOLONE DERIVATIVES

FIELD OF THE INVENTION

The present invention relates to new isoindolone derivatives of general formula:

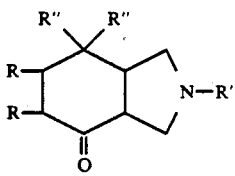

in which the radicals R represent hydrogen atoms or, together, form a bond, the symbol R' represents a hydrogen atom or a readily removable radical and the symbols R" are identical and represent phenyl radicals which can be substituted with a halogen atom or a methyl radical at the ortho or meta position, as well as their salts.

BACKGROUND OF THE INVENTION

U.S. Pat. No. 4,042,707 has previously described isoindole derivatives of general formula:

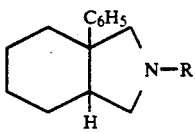

which are useful in the pharmaceutical field.

DETAILED DESCRIPTION OF THE INVENTION

The isoindolone derivatives according to the present invention are especially advantageous as intermediates for the preparation of products which are substance P antagonists.

In the general formula (I), when R' represents a readily removable group, this radical can advantageously be an allyl radical or a radical selected from the groups of structure:

in which $R_a$ and $R_b$ are hydrogen atoms or phenyl radicals, optionally substituted (with a halogen atom or an alkyl, alkyloxy or nitro radical), and $R_c$ is defined as $R_a$ and $R_b$ or represents an alkyl or alkyloxyalkyl radical, at least one $R_a$, $R_b$ and $R_c$ being a substituted or unsubstituted phenyl radical.

When the radicals defined by R" bear halogen substituents, the latter are advantageously selected from fluorine or chlorine. In addition, it is understood that the alkyl radicals mentioned above or which are mentioned below are linear or branched and contain, except where otherwise stated, 1 to 4 carbon atoms.

The products of general formula (I) possess stereoisomeric forms; it is understood that the isoindolone derivatives of (3aR,7aR) cis form in the pure state, or in the form of a mixture of the (3aRS,7aRS) cis forms, fall within the scope of the present invention.

According to the invention, the isoindolone derivative of general formula (I) may be obtained by a cycloaddition reaction, by the action of a silyl derivative of general formula:

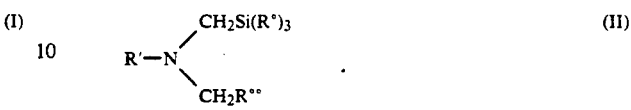

in which R' is the readily removable radical defined above, (R°)3 represents alkyl radicals or alkyl and phenyl radicals and R°° represents an alkyloxy, cyano or phenylthio radical, on a cyclohexenone derivative of general formula:

in which R and R" are defined as above, followed, where appropriate, by removal of the readily removable radical R' when it is desired to obtain an isoindolone of general formula (I) for which R' is a hydrogen atom.

The cycloaddition reaction is performed in the presence of a catalytic quantity of an acid in an organic solvent such as a chlorinated solvent, (e.g. dichloromethane, dichloroethane), in an aromatic hydrocarbon, in a nitrile (acetonitrile) or in an ether, at a temperature between 0° C. and the refluxing temperature of the reaction mixture.

The acids used are advantageously selected from trifluoroacetic acid, acetic acid, methanesulphonic acid or the acids mentioned in the references cited below for the preparation of the silyl derivatives of general formula (II).

The removal of the readily removable radical R', when it is desired to obtain an isoindolone for which R' is hydrogen, is performed by any known method which does not affect the remainder of the molecule.

In particular, when R is a hydrogen atom and when R' is other than an allyl radical, the group R' may be removed by catalytic hydrogenation in the presence of palladium. In general, the reaction is performed in an acid medium, in a solvent such as an alcohol (methanol, ethanol), in water or directly in acetic acid or formic acid, at a temperature of between 20° and 60° C.

When R' is a benzhydryl or trityl radical, the removal may be performed by treatment in an acid medium, working at a temperature between 0° C. and the refluxing temperature of the reaction mixture, in an alcohol, in an ether, in water or directly in acetic acid, formic acid or trifluoroacetic acid.

The group R' may also be removed by reaction with vinyl chloroformate, 1-chloroethyl chloroformate or phenyl chloroformate, proceeding via an intermediate product of general formula:

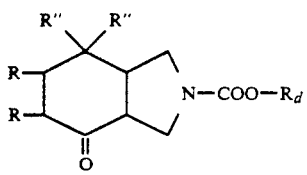

(IV)

in which R and R" are defined as above and $R_d$ is a vinyl, 1-chloroethyl or phenyl radical, followed by removal of the radical $R_d$ by acid treatment.

The action of the chloroformate is performed in an organic solvent such as a chlorinated solvent (e.g. dichloromethane, dichloroethane, chloroform), an ether (e.g. tetrahydrofuran, dioxane) or a ketone (e.g. acetone) or in a mixture of these solvents, at a temperature between 20° C. and the refluxing temperature of the reaction mixture. The removal of the radical $R_d$ is performed by treatment in an acid medium, e.g. with trifluoroacetic, formic, methanesulphonic, p-toluenesulphonic, hydrochloric or hydrobromic acid, in a solvent such as an alcohol, an ether, an ester, a nitrile or a mixture of these solvents or in water, at a temperature between 0° C. and the refluxing temperature of the reaction mixture. Under the conditions mentioned above for removal of the radicals R', the isoindolone derivative of general formula (I) is obtained in the state of a salt of the acid employed. The product may be liberated from its salt by the usual methods.

The silyl derivative of general formula (II) may be obtained according to the methods described by:

Y. Terao et al., Chem. Pharm. Bull., 33, 2762 (1985);
A. Hosomi et al., Chem. Lett., 1117 (1984);
A Padwa et al., Chem. Ber., 119, 813 (1986) or
Tetrahedron, 41 3529 (1985).

The cyclohexenone derivative of general formula (III) may be prepared as described below in the examples.

According to the invention, the isoindolone derivatives of general formula (I) may also be prepared by the action of an oxazolidinone of general formula:

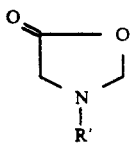

(V)

in which R' is a readily removable group as defined above, on a cyclohexenone of general formula (III), followed, where appropriate, by removal of the readily removable radical R' when it is desired to obtain an isoindolone derivative for which R' is a hydrogen atom.

The reaction is performed by heating to a temperature between 80° C. and the refluxing temperature of the reaction mixture, in a solvent such as an aromatic hydrocarbon (e.g. toluene or xylene), an ether (dioxane, glymes) or a halogenated solvent (e.g. trichloroethane, chlorobenzene).

Where appropriate, the removal of the radical R' is performed as described above.

The oxazolidinones of general formula (V) may be prepared according to, or by a method similar to, the method described by M. Joucla et al., Bull. Soc. Chim. Fr., 579 (1988).

According to the invention, the isoindolone derivatives of general formula (I) which R is a hydrogen atom, and R' is defined as above except for the possibility of representing a trityl radical, may also be obtained by a Mannich reaction starting with a derivative of general formula:

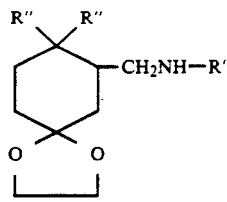

(VI)

in which R' and R" are defined as above.

The reaction is performed in an acid medium, in the presence of formaldehyde, at a temperature between 20° C. and the refluxing temperature of the reaction mixture, in a solvent such as an alcohol, (e.g. methanol, ethanol, isopropanol, polyethylene glycol) or an ether (e.g. dioxane, tetrahydrofuran, glyme).

It is advantageous to work in the presence of an inorganic or organic acid such as sulphuric, hydrochloric, methanesulphonic or p-toluenesulphonic acid.

When R' is other than a hydrogen atom, the amino derivative of general formula (VI) may be obtained from the derivative for which R' is a hydrogen atom, by any known method for the introduction of an amino-protecting radical which does not adversely affect the remainder of the molecule.

The reaction is performed, in particular, according to the methods described by T. W. Greene, Protective Groups in Organic Synthesis, A. Wiley, Interscience Publication (1981) or by McOmie, Protective Groups in Organic Chemistry, Plenum Press (1973).

When R' is a benzyl or substituted benzyl radical, it may be advantageous to prepare an amide of general formula:

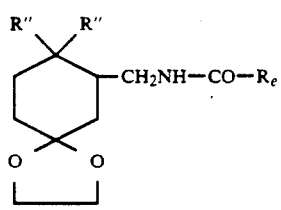

(VI)

in which R· is a phenyl or substituted phenyl radical, by the action of the corresponding acid chloride on the amine of general formula (VI) in which R' is a hydrogen atom, and then to reduce the amide obtained with lithium aluminium hydride in an anhydrous medium.

The preparation of the amide is performed, e.g., in the presence of a nitrogenous base such as triethylamine, in an anhydrous organic solvent (e.g. dichloromethane) at a temperature between of −20° and 40° C.

The reduction is performed in an organic solvent such as an ether (e.g. tetrahydrofuran), at a temperature between 0° C. and the refluxing temperature of the reaction mixture.

The amine of general formula (VI) for which R' is a hydrogen atom may be prepared from the cyclohexenone of the general formula (III) as described below in the examples.

According to the invention, the isoindolone derivatives of general formula (I) in which R and R' are hydrogen atoms may also be obtained by the catalytic hydrogenation of a 2-formyl-3-(nitromethyl)cyclohexanone of general formula:

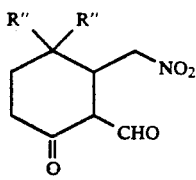

(VIII)

in which R" is defined as above.

The reaction is performed in an acid medium, in the presence of palladium.

It is advantageous to work under pressure in acetic acid at a temperature of between 20° and 80° C.

The 2-formyl-3-(nitromethyl)cyclohexanone of formula (VIII) may be obtained from 4,4'-diphenylcyclohexanone as described below in the examples.

According to the invention, when it is desired to obtain a product of general formula (I) of (3aR,7aR) form, the separation is performed according to known methods compatible with the molecule. By way of example, the separation of the isomers of the isoindolone derivative of general formula (I) for which R' is a hydrogen atom may be performed by the formation of a salt by means of an optically active acid (in particular L(+)- or D(−)-mandelic acid or dibenzoyltartaric acid), followed by separation of the isomers by crystallization. The desired isomer is liberated from its salt by treatment in a basic medium.

The new products of general formula (I), as well as their salts, are useful as intermediates for the preparation of isoindolone derivatives which antagonise the effects of substance P and corresponds to the general formula:

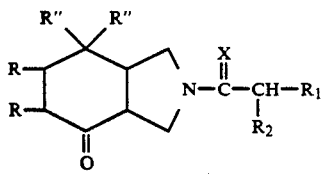

(IX)

in which
the radicals R are identical and represent hydrogen atoms or, together, form a bond,
the radicals R" are defined as above,
the symbol X represents an oxygen or sulphur atom or a radical N-R$_3$, for which R$_3$ is a hydrogen atom, an alkyl radical containing 1 to 12 carbon atoms, optionally substituted [with one or more carboxyl, dialkylamino, acylamino, carbamoyl, alkylcarbamoyl, dialkylcarbamoyl or alkyloxycarbonyl radicals (it being possible for the alkyl portions of these radicals to bear a dialkylamino or phenyl substituent) or with phenyl, substituted phenyl (substituted with halogen, alkyl, alkyloxy or dialkylamino), naphthyl, thienyl, furyl, pyridyl or imidazolyl radicals], or a dialkylamino radical,
the symbol R$_1$ represents a phenyl radical which is optionally substituted with one or more halogen atoms or hydroxyl radicals, alkyl radicals which can be optionally substituted (with halogen atoms or amino, alkylamino or dialkylamino radicals) or alkyloxy or alkylthio radicals which can be optionally substituted (with hydroxyl radicals or dialkyl- amino radicals in which the alkyl portions, with the nitrogen atom to which they are attached, can form a 5- to 6-membered heterocycle which can contain another hetero atom selected from oxygen, sulphur or nitrogen, optionally substituted with an alkyl radical), or which is substituted with amino or alkylamino radicals or dialkylamino radicals in which the alkyl portions, with the nitrogen atom to which they are attached, can form a heterocycle as defined above, or represents a cyclohexadienyl or naphthyl radical or a saturated or unsaturated, mono- or polycyclic heterocyclic radical containing 5 to 9 carbon atoms and one or more hetero atoms selected from oxygen, nitrogen or sulphur, and
the symbol R$_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino, acylamino or alkyloxycarbonylamino radical.

In the general formula (IX), the alkyl or acyl radicals contain 1 to 4 carbon atoms in a straight or branched chain; when R$_1$ or R$_3$ contains a halogen atom, the latter is selected from chlorine, bromine, fluorine and iodine; when R$_1$ represents a saturated or unsaturated, mono- or polycyclic heterocyclic radical, it may be selected, by way of example, from thienyl, furyl, pyridyl, dithiinyl, indolyl, isoindolyl, thiazolyl, isothiazolyl, oxazolyl, imidazolyl, pyrrolyl, triazolyl, thiadiazolyl, quinolyl, isoquinolyl and naphthyridinyl.

The isoindolone derivatives of general formula (IX) may be obtained by the action of the acid of general formula:

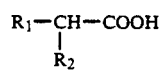

(X)

or a reactive derivative of this acid, in which R$_1$ and R$_2$ are defined as above, on an isoindole derivative of general formula (I) in which R' is a hydrogen atom and R" is defined as above, followed, where appropriate, by conversion of the amide obtained to a thioamide or an amidine for which X represents a radical N—R$_3$, R$_3$ having the definition given above.

It is understood that the amino, alkylamino or carboxyl radicals contained in R$_1$ and/or R$_2$ are preferably protected beforehand. The protection is performed with any compatible group whose introduction and removal do not affect the remainder of the molecule.

In particular, the protection is performed according to the methods described by T. W. Greene, Protective Groups in Organic Synthesis, A. Wiley—Interscience Publication (1981), or by McOmie, Protective Groups in Organic Chemistry, Plenum Press (1973).

By way of example,
the amino or alkylamino groups may be protected with methoxycarbonyl, ethoxycarbonyl, t-butoxycarbonyl, allyloxycarbonyl, vinyloxycarbonyl, trichloroethoxycarbonyl, trichloroacetyl, trifluoroacetyl, choroacetyl, trityl, benzhydryl, benzyl, allyl, formyl, acetyl or benzyloxycarbonyl radicals, or substituted derivatives of the latter;
the acid groups may be protected with methyl, ethyl, t-butyl, benzyl, substituted benzyl or benzhydryl radicals.

In addition, when $R_2$ represents a hydroxyl radical, it is preferable to protect this radical beforehand. The protection is performed, e.g. with an acetoxy, trialkylsilyl or benzyl radical or in the form of a carbonate.

When the condensation of the product of the general formula (II) is performed in its acid form (in which, where appropriate, the amino, alkylamino, carboxyl and/or hydroxyl substituents are protected beforehand), the reaction is generally performed in the presence of a condensing agent such as a carbodiimide (e.g. dicyclohexylcarbodiimide), N,N'-carbonyldiimidazole or 2-ethoxy-1-ethoxycarbonyl-1,2-dihydroquinoline, in an organic solvent such as a chlorinated solvent (e.g. dichloromethane, dichloroethane, chloroform), an ether (e.g. tetrahydrofuran, dioxane), an ester (e.g. ethyl acetate), an amide (e.g. dimethylacetamide, dimethylformamide), a nitrile (e.g. acetonitrile) or a ketone (e.g. acetone), or in an aromatic hydrocarbon such as, e.g., toluene, at a temperature of between $-20°$ and $40°$ C., and the product obtained is then converted, where appropriate, to a thioamide or an amidine and, where appropriate, the protective radicals are removed.

When the condensation of a reactive derivative of the acid of general formula (II) is performed, it is advantageous to employ the acid chloride, anhydride, a mixed anhydride or a reactive ester in which the remainder of the ester is a succinimido, 1-benzotriazolyl, 4-nitrophenyl, 2,4-dinitrophenyl, pentachlorophenyl or phthalimido radical. The reaction is generally performed at a temperature of between $-40°$ and $+40°$ C., in a chlorinated solvent, an ether, an amide, a ketone or a mixture of these solvents, in the presence of an acceptor for acid such as a nitrogenous organic base, an epoxide or a carbodiimide, or alternatively in an aqueous-organic medium in the presence of an alkaline condensing agent, and the amide obtained is then converted, where appropriate, to a thioamide and/or to an amidine as defined above.

The conversion of the amide of general formula (IX) to a thioamide is performed by any method of thionation which does not adversely affect the remainder of the molecule.

The conversion is performed, in particular, by the action of Lawesson's reagent [2,4-bis(4-methoxyphenyl)-2,4-dithioxo-1,3,2,4-dithiadiphosphetane] or by the action of phosphorus pentasulphide, in an organic solvent such as an ether (e.g. tetrahydrofuran, 1,2-dimethoxyethane, dioxane) or an aromatic hydrocarbon (e.g. toluene), at a temperature between $0°$ C. and the refluxing temperature of the reaction mixture.

The conversion of the amide of general formula (IX) to an amidine for which X is a radical N—$R_3$ is performed either directly or via the corresponding thioamide by preparing the isoindolium derivative of general formula:

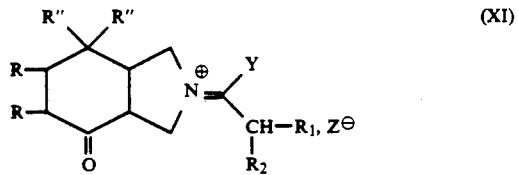

(XI)

in which R, R", $R_1$ and $R_2$ are defined as above, and either Y represents a chlorine atom or a methoxy or ethoxy radical and $Z^-$ represents a chloride, tetrafluoroborate, fluorosulphonate, trifluoromethylsulphonate, methyl sulphate or ethyl sulphate ion, or Y represents a chlorine atom or a methylthio, ethylthio, benzylthio or alkyloxycarbonylmethylthio radical and $Z^-$ is defined as above or represents an iodide or bromide ion, followed by reaction with an amine of general formula:

$$R_3-NH_2 \qquad (XII)$$

in which $R_3$ is defined as above.

The preparation of the isoindolium derivative of general formula (XI) in which Y is a chlorine atom or a methoxy or ethoxy radical is performed by the action of a reagent such as phosgene, phosphorus oxychloride, phosphorus pentachloride, thionyl chloride, oxalyl chloride, trichloromethyl chloroformate, triethyl(or trimethyl)oxonium fluoroborate, methyl(or ethyl) triflate, methyl(or ethyl) fluorosulphonate or methyl(or ethyl) sulphate. The preparation of the isoindolium derivative of general formula (XI) in which Y is a chlorine atom or a methyl(or ethyl)thio, benzylthio or alkyloxycarbonylmethylthio radical is performed starting with the isoindolone derivative of general formula (IX) in which X is a sulphur atom, by the action of a reagent as mentioned above or by the action of methyl, ethyl or benzyl bromide or iodide. The reaction is performed in a chlorinated solvent (e.g. dichloromethane, dichloroethane) or in an aromatic hydrocarbon (e.g. toluene), at a temperature between $0°$ C. and the refluxing temperature of the reaction mixture. When the reaction is performed starting with the thioamide of general formula (IX) it is also possible to use solvents such as ethers, ketones, esters or nitriles. The action of the amine of general formula (XII) on the derivative of general formula (XI) is performed in an anhydrous organic solvent such as a chlorinated solvent (e.g. dichloromethane, dichloroethane), in an alcohol/chlorinated solvent mixture, in an ether (e.g. tetrahydrofuran), in an ester (e.g. ethyl acetate), in an aromatic solvent (e.g. toluene) or in a mixture of these solvents, at a temperature between $-20°$ C. and the refluxing temperature of the reaction mixture.

It is not essential to have isolated the isoindolium derivative of general formula (XI) in order to employ it in this reaction.

The acids of general formula (X) may be prepared according to the methods described below in the examples, or by methods similar to these methods.

The new isoindolone derivatives of general formula (I), as well as the derivatives of general formula (IX), may be purified, where appropriate, by physical methods such as crystallization or chromatography. Where appropriate, the new products according to the invention may be converted to addition salts with acids. As examples, the salts formed with inorganic acids (hydrochlorides, hydrobromides, sulphates, nitrates, phosphates, tetrafluoroborates, fluorosulphonates) or with organic acids (succinates, fumarates, tartrates, acetates, propionates, maleates, citrates, methanesulphonates, p-toluenesulphonates, trifluoromethylsulphonates, methyl sulphates, ethyl sulphates or isethionates, or with substitution derivatives of these compounds) may be mentioned.

The isoindolone derivatives of general formula (IX) antagonise the effects of substance P, and as a result are especially advantageous in the fields of analgesia, inflammation, asthma and allergies, on the central nervous system, on the cardiovascular system, as an antispasmodic or on the immune system, as well as in the stimulation of lachrymal secretions. Their activity was demonstrated at doses of between 5 and 2000 nM in the technique described by C. M. Lee et al., Mol. Pharmacol., 23, 563–69 (1983).

Of special importance are the products of general formula (I) for which the radicals R are hydrogen atoms or, together, form a bond, the symbol R' is a hydrogen atom or a benzyl radical and the symbols R" are phenyl radicals optionally substituted at the ortho or meta position with fluorine or chlorine atoms or with a methyl radical.

The following products were shown to be especially advantageous:

- 7,7-diphenylperhydro-4-isoindolone, in its (3aR,7aR) or (3aRS,7aRS) forms, as well as its addition salts with acids;
- 7,7-bis(3-fluorophenyl)perhydro-4-isoindolone, in its (3aR,7aR) or (3aRS,7aRS) forms, as well as its addition salts with acids;
- 7,7-bis(2-fluorophenyl)perhydro-4-isoindolone, in its (3aR,7aR) or (3aRS,7aRS) forms, as well as its addition salts with acids;
- 7,7-bis(3-chlorophenyl)perhydro-4-isoindolone, in its (3aR,7aR) or (3aRS,7aRS) forms, as well as its addition salts with acids; and
- 7,7-bis(3-tolyl)perhydro-4-isoindolone, in its (3aR,-7aR) or (3aRS,7aRS) forms, as well as its addition salts with acids.

EXAMPLES

The examples which follow, given without implied limitation, illustrate the present invention.

In the examples which follow, it is understood that, except where otherwise stated, the proton NMR spectra were run at 250 MHz in dimethylsulphoxide; the chemical shifts are expressed in ppm.

EXAMPLE 1

Trifluoroacetic acid (5 drops) is added to a solution of 4,4-diphenyl-2-cyclohexen-1-one (155 g) and N-butoxymethyl-N-(trimethylsilylmethyl)benzylamine (202 cc) in dry dichloromethane (1000 cc), and the reaction mixture is heated to reflux for 45 minutes. N-Butoxymethyl-N-(trimethylsilylmethyl)benzylamine (50 cc) and trifluoroacetic acid (3 drops) are added and the mixture is stirred for a further 45 minutes under reflux before N-butoxymethyl-N-(trimethylsilylmethyl)benzylamine (25 cc) and trifluoroacetic acid (3 drops) are added again. The reaction mixture is stirred under reflux for 45 minutes, then treated with potassium carbonate (50 g), filtered and concentrated to dryness under reduced pressure (2.7 kPa). The residue is dissolved in isopropyl ether (200 cc) and the solution cooled to 0° C. for 1 hour. The crystals are drained, washed with isopropyl ether (2×15 cc) and dried to give (3aRS,7aRS)-2-benzyl-7,7-diphenylperhydro-4-isoindolone (193 g) in the form of white crystals, m.p. 132° C.

N-Butoxymethyl-N-(trimethylsilylmethyl)benzylamine may be prepared according to the method of Y. Terao et al., Chem. Pharm. Bull., 33, 2762 (1985).

EXAMPLE 2

(3aRS,7aRS)-2-Benzyl-7,7-diphenylperhydro-4-isoindolone (150 g), methanol (1500 cc) and 1N hydrochloric acid (450 cc) are added to palladinized charcoal (10% palladium) (15 g); the reaction mixture is hydrogenated with stirring at room temperature and at atmospheric pressure. After 5 hours' reaction, the theoretical volume of hydrogen has been absorbed; the reaction mixture is filtered, then concentrated to dryness under reduced pressure (2.7 kPa); the residue is crystallized in ethanol (200 cc). The crystals obtained are drained, washed with ethanol (50 cc) and dried. (3aRS,7aRS)-7,7-Diphenylperhydro-4-isoindolone hydrochloride (110 g), m.p. 270° C. with decomposition, is obtained.

Proton NMR spectrum: 2.03 (Mt, 1H, 1H of the H at position 5 or 6); 2.3 (Mt, 1H, 1H of the —H at position 5 or 6); 2.48 (DD, partially masked, 1H of the —CH$_2$— at position 1); 2.69 (DD, 1H, 1H of the —CH$_2$— at position 1); 2.8 (Mt, 2H, —CH$_2$— at position 6 or 5); 3.34 (DD, partially masked, 1H of the —CH$_2$— at position 3); 3.5 (Mt, 1H,

at position 3a); 3.82 (DD, 1H, 1H of the —CH$_2$— at position 3); 3.95 (Mt, 1H,

at position 7a); 7.15 to 7.65 (Mt, 10H, aromatic); 9.43 (Cx, 2H, —NH$_2$—Cl).

Infrared spectrum (KBr), characteristic bands in cm$^{-1}$: 3600–3300, 3100–3000, 3000–2850, 3100–2400, 1715, 1595, 1580, 1495, 1445, 1470, 775, 750, 705.

EXAMPLE 3

Vinyl chloroformate (56 cc) is added dropwise in the course of 10 minutes to a solution, cooled to +5° C., of (3aRS,7aRS)-2-benzyl-7,7-diphenylperhydro-4-isoindolone (193 g) in 1,2-dichloroethane (1225 cc). After stirring for 30 minutes at between 10° and 20° C., the reaction mixture is heated to reflux for 90 minutes, cooled and concentrated to dryness under reduced pressure (2.7 kPa then 1 kPa). The crystalline mass obtained is stirred vigorously with cold isopropyl ether (200 cc). The crystals obtained are drained, washed with isopropyl ether (2×100 cc) and dried. (3aRS,7aRS)-7,7-Diphenyl-2-vinyloxycarbonylperhydro-4-isoindolone (177 g), m.p. 178° C. is obtained.

(3aRS,7aRS)-7,7-Diphenyl-2-vinyloxycarbonylperhydro-4-isoindolone (177 g) is treated with a 5.7N solution (1000 cc) of hydrochloric acid in dry dioxane for 30 minutes at 20° C. The solution is concentrated to dryness under reduced pressure (2.7 kPa) and the residue taken up in ethanol (500 cc), and the reaction mixture is stirred at 60° C. for 30 minutes and then cooled to +5° C. The crystals obtained are drained, washed with ethanol (50 cc) and dried. (3aRS,7aRS)-7,7-Diphenylperhydro-4-isoindolone hydrochloride (130 g), m.p. 270° C. with decomposition, is obtained.

EXAMPLE 4

A mixture of 2-benzyl-7,7-diphenyl-2,3,3a,4,7,7a-hexahydro-1H-isoindol-4-one (3.4 g) and vinyl chloroformate (0.92 cc) in 1,2-dichloroethane (80 cc) is heated to reflux for 1 hour; the reaction mixture is concentrated to dryness under reduced pressure (2.7 kPa). The residue is crystallized in ethyl ether (20 cc). 7,7-Diphenyl-2-vinyloxycarbonyl-2,3,3a,4,7,7a-hexahydro-1H-isoindol-4-one (2.6 g), m.p. 162° C., is obtained.

7,7-Diphenyl-2-vinyloxycarbonyl-2,3,3a,4,7,7a-hexahydro-1H-isoindol-4-one (2.6 g) is stirred in a 3N solution (30 cc) of hydrogen chloride in dioxane at room temperature for 30 minutes; the mixture is concentrated to dryness under reduced pressure (2.7 kPa). The residue is taken up with ethanol (50 cc) and heated to reflux for 30 minutes; the mixture is concentrated to dryness under reduced pressure (2.7 kPa). The residue is crystallized in ethyl ether (20 cc); the crystals obtained are drained and dried. 7,7-Diphenyl-2,3,3a,4,7,7a-hexahydro-1H-isoindol-4-one hydrochloride (2 g), m.p. above 260° C., is obtained.

(3aRS,7aRS)-2-Benzyl-7,7-diphenyl-2,3,3a,4,7,7a-hexahydro-1H-isoindol-4-one may be obtained in the following manner:

Trifluoroacetic acid (2 drops) is added to a solution of 4,4-diphenyl-2,5-cyclohexadien-1-one (7.7 g) and N-butoxymethyl-N-(trimethylsilylmethyl)benzylamine (11 cc) in dry dichloromethane (80 cc), and the reaction mixture is heated to reflux for 1 hour and a half. A further portion (5 cc) of N-butoxymethyl-N-(trimethylsilylmethyl)benzylamine is added as well as trifluoroacetic acid (2 drops), and the reaction mixture is heated for 1 hour and a half. The reaction mixture is heated with potassium carbonate (3 g), filtered and concentrated to dryness under reduced pressure (2.7 kPa). The residue is crystallized in isopropyl ether (15 cc). The crystals obtained are drained, washed with isopropyl ether (2×5 cc) and dried; (3aRS,7aRS)-2-benzyl-7,7-diphenyl-2,3,3a,4,7,7a-hexahydro-1H-isoindol-4-one (4.4 g), m.p. 132° C., is obtained.

4,4-Diphenyl-2,5-cyclohexadien-1-one may be prepared according to the method of H. E. Zimmermann and D. I. Schuster J. Am. Chem. Soc., 84, 527 (1962).

EXAMPLE 5

Trifluoroacetic acid (3 cc) is added to a solution of 4,4-bis(3-fluorophenyl)cyclohexenone (90.3 g) and N-butoxymethyl-N-(trimethylsilylmethyl)benzylamine (123 cc) in dry dichloromethane (1000 cc). The reaction mixture is brought to reflux, then stirred for 2 hours while allowing the temperature to return to 25° C. and for a further 15 minutes after the addition of potassium carbonate (60 g). After filtration and concentration to dryness under reduced pressure (2.7 kPa), the crystallized residue is stirred vigorously with isopropyl ether, drained, washed and recrystallized in cyclohexane (300 cc). The crystals are drained, washed with cyclohexane (2×15 cc) and dried to give (3aRS,7aRS)-2-benzyl-7,7-bis(3-fluorophenyl)perhydro-4-isoindolone (92 g) in the form of white crystals. M.p. 124° C.

Butenone (50.4 cc) is added to a solution of bis(3-fluorophenyl)acetaldehyde (144.5 g) in ethyl ether (500 cc), and then, after cooling to 0° C., a solution of potassium hydroxide (13.9 g) in ethanol (89 cc) is added dropwise. The reaction mixture is stirred for 2 h at 0° C. and then for 16 hours at 25° C. and diluted with ethyl acetate (300 cc) and water (500 cc). The aqueous phase is washed with ethyl acetate (300 cc). The combined organic phases are washed with a saturated sodium chloride solution (500 cc), dried over magnesium sulphate and concentrated under reduced pressure (2.7 kPa). The residue is chromatographed (in two runs) on silica gel (particle size 0.04–0.063 mm, columns 8.5 cm in diameter, 34 cm high), eluting under a nitrogen pressure of 0.5 bar with a mixture of cyclohexane and ethyl acetate (90:10). 4,4-Bis(3-fluorophenyl)cyclohexanone (90.3 g) is obtained in the form of white crystals. M.p. 95° C.

A solution of 1,1-bis(3-fluorophenyl)-2-methoxyethanol (156.7 g) (obtained by the reaction of 3-fluorophenylmagnesium bromide with methyl 2-methoxyacetate in THF) in formic acid (160 cc) is heated to reflux for 16 hours, cooled and poured into a mixture of saturated sodium carbonate solution (800 cc) and ethyl acetate (500 cc). The organic phase is washed with water (2×500 cc) and with saturated sodium chloride solution (500 cc), then dried and concentrated to dryness under reduced pressure (2.7 kPa) to give bis(3-fluorophenyl)acetaldehyde (144.5 g) in the form of a yellow oil.

EXAMPLE 6

A solution of (3aRS,7aRS)-2-benzyl-7,7-bis(3-fluorophenyl)perhydro-4-isoindolone (92.2 g) in 1,2-dichloroethane (860 cc) is treated with vinyl chloroformate (26.3 cc) and heated to reflux for 3 hours, then concentrated under reduced pressure (2.7 kPa). The residue is chromatographed (in two runs) on silica gel (particle size 0.04–0.063 mm, columns 8 cm in diameter and 35 cm high), eluting under a nitrogen pressure of 0.5 bar with a mixture of cyclohexane and ethyl acetate (75:25). The meringue-like product obtained is crystallized in isopropyl ether to give (3aRS,7aRS)-7,7-bis(3-fluorophenyl)-2-vinyloxycarbonylperhydro-4-isoindolone (50.3 g). M.p. 152° C.

(3aRS,7aRS)-7,7-Bis(3-fluorophenyl)-2-vinyloxycarbonylperhydro-4-isoindolone (64.5 g) is treated with a 6N solution (330 cc) of hydrochloric acid in dioxane for 30 minutes at 25° C. The solution is concentrated to dryness under reduced pressure (2.7 kPa) and the residue taken up with ethanol (500 cc). The solution is heated to 60° C. for 6 hours and stirred for 16 hours at 25° C., then concentrated to one half under reduced pressure (2.7 kPa), and the crystals formed are drained and washed with isopropyl ether, then dried. 7,7-Bis(3-fluorophenyl)perhydro-4-isoindolone hydrochloride (48.7 g) is obtained. M.p. 264° C.

EXAMPLE 7

Trifluoroacetic acid (3 drops) is added to a solution of 4,4-bis(2-fluorophenyl)cyclohexenone (4.3 g) and N-butoxymethyl-N-(trimethylsilylmethyl)benzylamine (5.8 cc) in dry dichloromethane (30 cc). The reaction mixture is brought to reflux and then stirred for 16 hours after the temperature has been allowed to return to 25° C. N-Butoxymethyl-N-(trimethylsilylmethyl)benzylamine (2.5 cc) and trifluoroacetic acid (3 drops) are added and the mixture is stirred for 3 hours under reflux. The reaction mixture is treated with potassium carbonate (3 g) and stirred for 15 minutes. After filtration and concentration to dryness under reduced pressure (2.7 kPa), the residue is chromatographed on a column of silica gel (particle size 0.04–0.063 mm, diameter 4 cm, height 32 cm), eluting under a nitrogen pressure of 0.5 bar with a mixture of cyclohexane and ethyl acetate (85:15) and collecting 20-cc fractions. Fractions 13 to 22 are combined and concentrated to dryness under reduced pressure (2.7 kPa) to give (3aRS,7aRS)-2-benzyl-7,7-bis(2-fluorophenyl)perhydro-4-isoindolone (2.28 g). M.p. 138° C.

4,4-Bis(2-fluorophenyl)cyclohexenone may be prepared in the following manner:

Potassium carbonate (26.9 g) is added to a solution of bis(2-fluorophenyl)acetaldehyde (30.8 g) in 1,2-dimethoxyethane (135 cc), and butenone (19.9 cc) is then added dropwise and after cooling to −50° C. The reaction mixture is stirred for 12 h at −50° C. and then for 6 hours at 25° C. and diluted with ethyl acetate (250 cc) and water (200 cc). The organic phase is washed with water (3×200 cc) and then with saturated sodium chloride solution (200 cc), dried over magnesium sulphate and concentrated under reduced pressure (2.7 kPa). The residue is chromatographed on a column of silica gel (particle size 0.04–0.063 mm, diameter 5.5 cm, height 50 cm), eluting under a nitrogen pressure of 0.5 bar with a mixture of cyclohexane and ethyl acetate (90:10). 2,2-Bis(2-fluorophenyl)-5-oxohexanal (9 g) is obtained in the form of a yellow oil. A solution of this compound (6.65 g) in toluene (100 cc) containing para-toluenesulphonic acid (1.5 g) is heated to reflux for 3 hours, washed with water (2×100 cc) and then with saturated sodium chloride solution (100 cc), dried over magnesium sulphate and concentrated under reduced pressure (2.7 kPa). The residue is chromatographed on a column of silica gel (particle size 0.04–0.063 mm, diameter 4 cm, height 30 cm), eluting under a nitrogen pressure of 0.5 bar with a mixture of cyclohexane and ethyl acetate (90:10) and collecting 15-cc fractions. Fractions 21 to 26 are combined and concentrated to dryness under reduced pressure (2.7 kPa) to give 4,4-bis(2-fluorophenyl)cyclohexenone (2.83 g) in the form of a yellow oil.

Proton NMR spectrum (DMSO-$d_6$): 2.6 (m, 2H, —CH$_2$— at position 5); 2.8 (broad dd, 2H, —CH$_2$— at position 6); 6.2 (d, 1H, H at position 2); 6.9 to 7.4 (m, 9H aromatic and H at position 3).

Bis(2-fluorophenyl)acetaldehyde may be prepared in the following manner:

A solution of 1,2-bis(2-fluorophenyl)oxirane (26.3 g) in toluene (500 cc) is treated dropwise with boron trifluoride etherate (7 cc) and stirred for 2 hours at 25° C., then washed with water (50 cc) and saturated sodium bicarbonate solution (50 cc). After drying over magnesium sulphate and concentration to dryness under reduced pressure (2.7 kPa), bis(2-fluorophenyl)acetaldehyde (25 g) is obtained in the form of a yellow oil.

1,2-Bis(2-fluorophenyl)oxirane may be prepared according to the method described by V. Mark (J. Am. Chem. Soc., 85, 1884 (1963)).

EXAMPLE 8

A solution of (3aRS,7aRS)-2-benzyl-7,7-bis(2-fluorophenyl)perhydro-4-isoindolone (2.34 g) in methanol (100 cc), to which N hydrochloric acid (6.2 cc) is added, is hydrogenated at atmospheric pressure in the presence of palladinized charcoal (10% palladium) (0.4 g) for 5 hours at 25° C. The reaction medium is filtered and concentrated under reduced pressure (2.7 kPa) to give (3aRS,7aRS)-7,7-bis(2-fluorophenyl)perhydro-4-isoindolone hydrochloride (2 g) in the form of a white solid.

Proton NMR spectrum (DMSO-$d_6$): 2 to 2.4 (m, 2H, —CH$_2$— at position 5); 2.7 to 3 (m, 4H, —CH$_2$— at positions 1 and 6); 3.5 (broad dd, 1H, 1H at position 3); 3.7 (broad dd, 1H, H at position 3a); 3.9 (broad d, 1H, 1H at position 3); 4.2 (m, 1H, H at position 7a); 7.1 to 8 (m, 8H aromatic).

EXAMPLE 9

Trifluoroacetic acid (15 drops) is added to a solution of 4,4-bis(3-chlorophenyl)cyclohexenone (26.8 g) and N-butoxymethyl-N-(trimethylsilylmethyl)benzylamine (33 cc) in dry dichloromethane (200 cc). The reaction mixture is brought to reflux, then stirred for 16 hours after the temperature has been allowed to return to 25° C. and for a further 15 minutes after the addition of potassium carbonate (16 g). After filtration and concentration to dryness under reduced pressure (2.7 kPa), the residue is chromatographed on a column of silica gel (particle size 0.04–00063 mm, diameter 7 cm, height 40 cm), eluting under a nitrogen pressure of 0.5 bar with a mixture of cyclohexane and ethyl acetate (75:25) and collecting 500-cc fractions. Fractions 12 to 18 are combined and concentrated to dryness under reduced pressure (2.7 kPa) to give (3aRS,7aRS)-2-benzyl-7,7-bis(3-chlorophenyl)perhydro-4-isoindolone (16.2 g) in the form of a yellow oil.

Proton NMR spectrum (DMSO-$d_6$): [1.75 (ddd, 1H) and 2.1 to 2.45 (m, 3H): —CH$_2$— at positions 5 and 6]; 2.7 to 2.9 (m, 4H, —CH$_2$— at positions 1 and 3); 3.1 (m, 1H, H at position 3a); 3.5 (AB, 2H, benzyl-CH$_2$—); 3.8 (broad dd, 1H, H at position 7a); 7.1 to 7.5 (m, 13H aromatic).

Butenone (11.3 cc) is added to a solution of bis(3-chlorophenyl)acetaldehyde (36.9 g) in ethyl ether (200 cc), and then, after cooling to 0° C., a solution of potassium hydroxide (3.1 g) in ethanol (20 cc) is added dropwise. The reaction mixture is stirred for 2 h at 0° C. and then for 16 hours at 25° C. and diluted with ethyl acetate (100 cc) and water (200 cc). The aqueous phase is washed with ethyl acetate (100 cc). The combined organic phases are washed with saturated sodium chloride solution (3×100 cc), dried over magnesium sulphate and concentrated under reduced pressure (2.7 kPa). The residue is chromatographed on a column of silica gel (particle size 0.04–0.063 mm, diameter 7 cm, height 42 cm), eluting under a nitrogen pressure of 0.5 bar with a mixture of cyclohexane and ethyl acetate (90:10). 4,4-Bis(3-chlorophenyl)cyclohexenone (27.7 g) is obtained in the form of a yellow oil.

Proton NMR spectrum (DMSO-$d_6$): 2.3 (broad dd, 2H, —CH$_2$— at position 5); 2.7 (broad dd, 2H, —CH$_2$— at position 6); 6.2 (d, 1H, H at position 2); 7.2 to 7.4 (m, 8H aromatic); 7.6 (d, 1H, H at position 3).

A solution of 1,1-bis(3-chlorophenyl)-2-methoxyethanol (47 g) (obtained by the reaction of 3-chlorophenylmagnesium bromide with methyl 2-methoxyacetate in THF) in formic acid (44 cc) is heated to reflux for 5 hours, cooled and poured into a mixture of saturated sodium carbonate solution (500 cc) and ethyl acetate (300 cc). The organic phase is washed with water (3×250 cc) and with saturated sodium chloride solution (200 cc), then dried and concentrated to dryness under reduced pressure (2.7 kPa) to give bis(3-chlorophenyl)acetaldehyde (36.9 g) in the form of a yellow oil.

EXAMPLE 10

A solution of (3aRS,7aRS)-2-benzyl-7,7-bis(3-chlorophenyl)perhydro-4-isoindolone (11.5 g) in 1,2-dichloroethane (250 cc) is treated with vinyl chloroformate (2.8 cc) and heated to reflux for 16 hours, then concentrated under reduced pressure (2.7 kPa). The residue is chromatographed on a column of silica gel (particle size 0.04–0.063 mm, diameter 6 cm, height 32 cm), eluting under a nitrogen pressure of 0.5 bar with a mixture of cyclohexane and ethyl acetate (80:20) and collecting 25-cc fractions. Fractions 19 to 27 are combined and concentrated to dryness under reduced pressure (2.7 kPa). The meringue-like product obtained is solidified in isopropyl ether and the precipitate is drained, washed with isopropyl ether and dried to give (3aRS,7aRS)-7,7-bis(3-chlorophenyl)-2-vinyloxycarbonylperhydro-4-isoindolone (6.7 g) in the form of a white solid.

Proton NMR spectrum (DMSO-$d_6$): 2.1 and 2.3 (2 broad ddd, 2H, —CH$_2$— at position 5); 2.7 to 3 (m, 4H, —CH$_2$— at positions 1 and 6); 3.3 (m, 1H, H at position 3a); 3.45 (broad dd, 1H, 1H at position 3); 4.1 (m, 2H, H at position 7a and 1H at position 3); 4.45 and 4.70 (2 broad d, 2H, vinyl=CH$_2$); 7.05 (dd, 1H, vinyl OCH=); 7.2 to 7.7 (m, 8H aromatic).

(3aRS,7aRS)-7,7-Bis(3-chlorophenyl)-2-vinyloxycarbonylperhydro-4-isoindolone (1.5 g) is treated with a 6N solution (7.4 cc) of hydrochloric acid in dioxane for 2 hours at 25° C. The solution is concentrated to dryness under reduced pressure (2.7 kPa) and the residue is heated for 1 hour in solution in ethanol at 60° C. and then stirred for 6 hours at 25° C. The solution is concentrated to dryness under reduced pressure (2.7 kPa) and the meringue-like product obtained solidified in isopropyl ether. The precipitate is drained and washed with isopropyl ether, then dried to give 7,7-bis(3-chlorophenyl)perhydro-4-isoindolone hydrochloride (1 g).

Proton NMR spectrum (DMSO-$d_6$): 2 to 2.4 (m, 2H, —CH$_2$— at position 5); 2.55 to 2.9 (m, 2H, —CH$_2$— at position 6); 3.3 (broad dd, 1H, at position 3); 3.5 (m, 1H, H at position 3a); 3.85 (broad d, 1H, 1H at position 3); 3.95 (m, 1H, H at position 7a); 7.1 to 7.76 (m, 8H aromatic).

EXAMPLE 11

Trifluoroacetic acid (12 drops) is added to a solution of 4,4-bis(3-tolyl)cyclohexenone (16.7 g) and N-butoxymethyl-N-(trimethylsilylmethyl)benzylamine (18.7 cc) in dry dichloromethane (150 cc). The reaction mixture is brought to reflux, then stirred for 3 hours while allowing the temperature the return to 25° C. and for a further 10 minutes after the addition of potassium carbonate (12 g). After filtration and concentration to dryness under reduced pressure (2.7 kPa), the residue is chromatographed on a column of silica gel (particle size 0.04–0.063 mm, diameter 5 cm, height 50 cm), eluting under a nitrogen pressure of 0.7 bar with a mixture of cyclohexane and ethyl acetate (85:15) and collecting 25-cc fractions. Fractions 14 to 30 are combined and concentrated to dryness under reduced pressure (2.7 kPa) to give (3aRS,7aRS)-2-benzyl-7,7-bis(3-tolyl)perhydro-4-isoindolone (13.9 g) in the form of a colorless oil.

Proton NMR spectrum (CDCl$_3$): [1.98 (ddd, 1H) and 2.2 to 2.5 (m, 3H): —CH$_2$— at positions 5 and 6]; (s, 6H, ArCH$_3$); 2.5 to 3.05 (m, 4H, —CH$_2$— at positions 1 and 3); 3.2 (m, 1H, H at position 3a); 3.45 and 3.65 (AB, 2H, Ar —CH$_2$—); 3.7 (m, 1H, H at position 7a); 6.9 to 7.4 (m, 13H aromatic).

4,4-Bis(3-tolyl)cyclohexenone may be prepared in the following manner:

Butenone (7.23 cc) is added to a solution of bis(3-tolyl)acetaldehyde (20.4 g) in ethyl ether (110 cc) and then, after cooling to 0° C., a solution of potassium hydroxide (2 g) in ethanol (12.7 cc) is added dropwise. The reaction mixture is stirred for 2 hours at 0° C. and then for 16 hours at 25° C. and diluted with ethyl acetate (200 cc) and water (200 cc). The aqueous phase is washed with ethyl acetate (2×250 cc). The combined organic phases are washed with water (2×250 cc) and then with saturated sodium chloride solution (250 cc), dried over magnesium sulphate and concentrated under reduced pressure (2.7 kPa). The residue is chromatographed on silica gel (particle size 0.04–0.063 mm, column 5.4 cm in diameter and 40 cm high), eluting under a nitrogen pressure of 0.5 bar with a mixture of cyclohexane and ethyl acetate (85:15). 4,4-Bis(3-tolyl)cyclohexenone (16.7 g) is obtained in the form of a yellow oil.

Proton NMR spectrum (CDCl$_3$): 2.36 (s, 6H, ArCH$_3$); 2.45 (broad dd, 2H, —CH$_2$— at position 6); 2.72 (broad dd, 2H, —CH$_2$— at position 5); 6.23 (d, 1H, H at position 2); 7 to 7.3 (m, 8H aromatic); 7.34 (d, 1H, H at position 3).

Bis(3-tolyl)acetaldehyde may be prepared in the following manner:

A solution of 1,1-bis(3-tolyl)-2-methoxyethanol (24.66 g) (obtained by the reaction of 3-tolylmagnesium bromide with methyl 2-ethoxyacetate in tetrahydrofuran) in formic acid (30 cc) is heated to reflux for 12 hours, cooled and poured into a mixture of saturated sodium carbonate solution (400 cc) and ethyl acetate (400 cc). The organic phase is washed with water (3×300 cc) and with saturated sodium chloride solution (300 cc) then dried and concentrated to dryness under reduced pressure (2.7 kPa) to give bis(3-tolyl)acetaldehyde (20.45 g) in the form of a yellow oil.

EXAMPLE 12

A solution of (3aRS,7aRS)-2-benzyl-7,7-bis(3-tolyl)-perhydro-4-isoindolone (13.7 g) in 1,2-dichloroethane (150 cc) is treated with vinyl chloroformate (3.7 cc) and heated to reflux for 3 hours, then concentrated under reduced pressure (2.7 kPa). The residue is chromatographed on silica gel (particle size 0.04–0.063 mm, column 5.4 cm in diameter and 39 cm high), eluting under a nitrogen pressure of 0.5 bar with a mixture of cyclohexane and ethyl acetate (80:20). Fractions 23 to 39 are combined and concentrated to dryness under reduced pressure (2.7 kPa) to give (3aRS,7aRS)-7,7-bis(3-tolyl)-2-vinyloxycarbonylperhydro-4-isoindolone (7.4 g) in the form of a white meringue-like product.

Proton NMR spectrum (DMSO-$d_6$/AcOD 90:10):

At room temperature, a mixture of the two rotamers is observed. 1.95 to 2.4 (m, 2H, —CH$_2$— at position 5); 2.27 and 2.32 (2 s, 6H, ArCH$_3$); 2.4 to 2.95 (m, 4H, —CH$_2$— at positions 1 and 6); 3.2 to 3.5 (m, 2H, H at position 3a and 1H at position 3); 4.03 (m, 1H, H at position 7a); 4.09 and 4.16 (2 broad d, 1H, H at position 3); 4.35 to 4.85 (4 broad d, 2H, vinyl=CH$_2$); 6.9 to 7.5 (m, 9H, aromatic and vinyl OCH=).

(3aRS,7aRS)-7,7-Bis(3-tolyl)-2-vinyloxycarbonylperhydro-4-isoindolone (7.4 g) is treated with a 6N solution (39 cc) of hydrochloric acid in dioxane for 30 minutes at 25° C. The solution is concentrated to dryness under reduced pressure (2.7 kPa) and the residue taken up with ethanol (100 cc). The solution is heated to 60° C. for 2 hours and stirred for 16 hours at 25° C., then concentrated to dryness under reduced pressure (2.7 kPa). The residue is solidified with isopropyl ether and the solid is washed, drained and dried. 7,7-Bis(3-tolyl)perhydro-4-isoindolone hydrochloride (6.36 g) is obtained in the form of a yellow solid.

Proton NMR spectrum (DMSO-$d_6$/AcOD 90:10): 1.95 to 2.35 (m, 2H, —CH$_2$— at position 5); 2.24 and 2.3 (2 s, 6H, ArCH$_3$); 2.4 to 2.9 (m, 4H, —CH$_2$— at positions 6 and 1); 3.3 (broad dd, 1H, 1H at position 3); 3.48 (m, 1H, H at position 3a); 3.85 (broad d, 1H, 1H at position 3); 3.90 (m, 1H, H at position 7a); 6.9 to 7.4 (m, 8H aromatic).

EXAMPLE 13

A solution of 4,4-diphenyl-2-cyclohexen-1-one (25 g) and 3-benzyl-5-oxazolidone (2.5 g) in dry toluene (100 cc) is heated to reflux for 2 hours 30 minutes. The reaction mixture is concentrated to dryness under reduced pressure (2.7 kPa). The residue is chromatographed on a column of silica gel (0.2–0.063 mm, diameter 4.5 cm, height 23 cm), eluting under a nitrogen pressure of 0.5 bar with a mixture of cyclohexane and ethyl acetate (80:20 by volume) and collecting 50-cc fractions. Fractions 13 to 17 are combined and concentrated to dryness under reduced pressure (2.7 kPa) to give (3aRS,7aRS)-2-benzyl-7,7-diphenylperhydro-4-isoindolone (0.9 g) in the form of white crystals, m.p. 132° C.

3-Benzyl-5-oxazolidinone may be prepared according to the method of M. Joucla and J. Mortier, Bull. Soc. Chim. Fr., 579 (1988).

EXAMPLE 14

A solution of (RS)-6-benzylaminomethyl-7,7-diphenyl-1,4-dioxaspiro[4.5]decane (0.41 g) in ethanol (0.4 cc) is added to a solution, brought to reflux, of paraformaldehyde (0.14 g) in 2% strength aqueous sulphuric acid solution (20 cc), and heating to reflux is continued for 48 hours. The reaction mixture is cooled to +25° C., alkalinized with 4N aqueous sodium hydroxide solution (5 cc) and extracted with ethyl acetate (4×40 cc) and the organic phases are combined, washed with distilled water (100 cc), dried over magnesium sulphate, filtered and concentrated to dryness under reduced pressure (2.7 kPa). The residue is chromatographed on a column of silica gel with a slight excess pressure of nitrogen (0.04–0.063 mm, diameter 2 cm, height 15 cm), eluting with a mixture of cyclohexane and ethyl acetate (60:40 by volume) and collecting 20-cc fractions. Fractions 4 and 5 are combined and concentrated to dryness under reduced pressure (2.7 kPa). (3aRS,7aRS)-2-Benzyl-7,7-diphenylperhydro-4-isoindolone (0.23 g) is obtained in the form of white crystals, m.p. 132° C.

(RS)-6-Benzylaminomethyl-7,7-diphenyl-1,4-dioxaspiro[4.5]decane may be prepared in the following manner:

A solution of (RS)-6-benzamidomethyl-7,7-diphenyl-1,4-dioxaspiro[4.5]decane (8.1 g) in anhydrous tetrahydrofuran (150 cc) is added dropwise, in the course of 1 hour 30 minutes and while the temperature of the reaction mixture is maintained at +5° C., to a suspension, cooled to +5° C. of lithium aluminum hydride (1.9 g) in anhydrous tetrahydrofuran (60 cc), and the mixture is then brought to reflux for 24 hours. The reaction mixture is then cooled to +5° C., treated with distilled water (2.1 cc), then with 5N aqueous sodium hydroxide solution (1.9 cc) and then with distilled water (5.8 cc), filtered and concentrated to dryness under reduced pressure (2.7 kPa). The residue is chromatographed on a column of silica gel with a slight excess pressure of nitrogen (0.04–0.063 mm, diameter 5 cm, height 29 cm), eluting with ethyl acetate and collecting 120-cc fractions. Fractions 3 to 12 are combined and concentrated to dryness under reduced pressure (2.7 kPa). (RS)-6-Benzylaminomethyl-7,7-diphenyl-1,4-dioxaspiro[4.5]decane (6.6 g) is obtained in the form of a yellow oil.

(RS)-6-Benzamidomethyl-7,7-diphenyl-1,4-dioxaspiro[4.5]decane may be prepared in the following manner:

A solution of benzoyl chloride (7.7 g) in anhydrous dichloromethane (10 cc) is added dropwise, in the course of 40 minutes and while the temperature of the reaction mixture is maintained at +5° C., to a solution, cooled to +5° C., of (RS)-6-aminomethyl-7,7-diphenyl-1,4-dioxaspiro[4.5]decane (16.2 g) and triethylamine (5.6 g) in anhydrous dichloromethane (150 cc). The reaction mixture is then stirred for 4 hours at +25° C., thereafter washed with distilled water (125 cc) cooled to +5° C., dried over magnesium sulphate, filtered and concentrated to dryness under reduced pressure (2.7 kPa). The residue is recrystallized in a mixture (50 cc) of acetonitrile and isopropyl ether (50:50 by volume). The crystals are drained and dried. (RS)-6-Benzamidomethyl-7,7-diphenyl-1,4-dioxaspiro[4.5]decane (16 g) is obtained in the form of white crystals. M.p. 162° C.

(RS)-6-Aminomethyl-7,7-diphenyl-1,4-dioxaspiro[4.5]decane may be prepared in the following manner:

A solution of (RS)-6-nitromethyl-7,7-diphenyl-1,4-dioxaspiro[4.5]decane (63 g) in anhydrous tetrahydrofuran (300 cc) is added dropwise in the course of 1 hour to a suspension, cooled to +5° C., of lithium aluminium hydride (8.13 g) in anhydrous tetrahydrofuran (250 cc) while the temperature of the reaction mixture is maintained at +5° C., and the mixture is then brought to reflux for 2 hours. The reaction mixture is then cooled to +5° C., treated with distilled water (8.93 cc), then with 5N aqueous sodium hydroxide solution (8 cc) and then with distilled water (25 cc), filtered and concentrated to dryness under reduced pressure (2.7 kPa). The residue is chromatographed on a column of silica gel with a slight excess pressure of nitrogen (0.04–0.063 mm, diameter 6.5 cm, height 45 cm), eluting with a mixture of dichloromethane and methanol (90:10) by volume) and collecting 120-cc fractions. Fractions 10 to 31 are combined and concentrated to dryness under reduced pressure (2.7 kPa). (RS)-6-Aminomethyl-7,7-diphenyl-1,4-dioxaspiro[4.5]decane (16.5 g) is obtained in the form of an orange-colored oil.

(RS)-6-Nitromethyl-7,7-diphenyl-1,4-dioxaspiro[4.5]decane may be prepared in the following may be prepared in the following manner:

A solution of 3-nitromethyl-4,4-diphenylcyclohexanone (69 g), ethylene glycol (30.48 g) and chlorotrimethylsilane (106.8 g) in anhydrous methylene chloride (1 liter) is brought to reflux for 2 hours, then cooled to +25° C., washed with saturated aqueous sodium hydrogen carbonate solution (600 cc) and then with saturated aqueous sodium chloride solution (300 cc), dried over magnesium sulphate, filtered and concentrated to dryness under reduced pressure (2.7 kPa). The residue is chromatographed on a column of silica gel with a slight excess pressure of nitrogen (0.04–0.063 mm, diameter 6.5 cm, height 45 cm), eluting with a mixture of cyclohexane and ethyl acetate (90:10 by volume) and collecting 500-cc fractions. Fractions 1 to 3 are combined and concentrated to dryness under reduced pressure (2.7 kPa). (RS)-6-Nitromethyl-7,7-diphenyl-1,4-dioxaspiro[4.5]decane (63.3 g) is obtained in the form of white crystals, m.p. 148° C.

(RS)-3-Nitromethyl-4,4-diphenylcyclohexanone may be prepared in the following manner:

A solution (11.45 g) of benzyltrimethylammonium hydroxide in methanol is added to a solution of 4,4-diphenyl-2-cyclohexenone (60 g) and nitromethane (14.75 g) in 2-methyl-2-propanol (400 cc) and anhydrous tetrahydrofuran (200 cc), and the reaction mixture is stirred at +25° C. for 144 hours: a crystalline solid precipitates slowly. This suspension is filtered and the crystals are washed with petroleum ether (50 cc) cooled to 0° C., drained and dried. (RS)-3-Nitromethyl-4,4-diphenylcyclohexanone (69.1 g) is obtained in the form of white crystals, m.p. 164° C.

EXAMPLE 15

A solution of (RS)-6-aminomethyl-7,7-diphenyl-1,4-dioxaspiro[4.5]decane (1 g) in ethanol (2 cc) is added to a solution, brought to reflux, of paraformaldehyde (0.09 g) in 2% strength aqueous sulphuric acid solution (5 cc), and heating to reflux is continued for 48 hours. The reaction mixture is then cooled to +5° C., alkalinized with 4N aqueous sodium hydroxide solution and extracted with dichloromethane (3×50 cc), and the organic phases are combined, washed with distilled water (100 cc), dried over magnesium sulphate, filtered and concentrated to dryness under reduced pressure (2.7 kPa). The residue is dissolved in acetone (8 cc), and this solution is acidified with 3.6N ethereal hydrogen chloride (2 cc) and concentrated to dryness under reduced pressure (2.7 kPa). The residue is chromatographed on a column of silica gel with a slight excess pressure of nitrogen (0.04–0.063 mm, diameter 2.5 cm, height 35 cm), eluting with a mixture of dichloromethane and methanol (85:15) by volume) and collecting 15-cc fractions. Fraction 9 is concentrated to dryness under reduced pressure (2.7 kPa) and dissolved in water (10 cc), this aqueous solution is alkalinized at +5° C. with 4N aqueous sodium hydroxide solution and extracted with dichloromethane (3×30 cc), and the organic phases are combined, washed with distilled water (50 cc), dried over magnesium sulphate, filtered and concentrated to dryness under reduced pressure. (3aRS,7aRS)-7,7-Diphenylperhydro-4-isoindolone (0.07 g) is obtained in the form of a white meringue-like product.

Proton NMR spectrum: 2.15 and 2.4 (2 Mt, 1H each, respectively, —CH₂— at position 6); 2.75 (Mt, 4H, —CH₂— at position 1 and —CH₂— at position 5); 3.3 to 3.6 (Mt, 2H, 1H of the —CH₂— at position 3 and

at position 3a); 3.95 to 4.2 (Mt, 2H, 1H of the —CH₂— at position 3 and

at position 7a); 7 to 7.5 (Mt, 10H, aromatic).

Infrared spectrum (CHBr₃), characteristic bands (cm⁻¹): 3350, 3100–3000, 3000–2800, 1705; 1600, 1580, 1495, 1460, 1445, 755.

EXAMPLE 16

A solution of 4,4-diphenyl-2-formyl-3-(nitromethyl)-cyclohexanone (1.7 g) in acetic acid (50 cc) is hydrogenated in the presence of palladinized charcoal (10% palladium) (0.2 g) at 50° C. and under a pressure of 50 bars. After 5 hours' reaction, the reaction mixture is filtered and then concentrated to dryness under reduced pressure (2.7 kPa); the residue is taken up with ethyl acetate (100 cc) and this solution is washed with water (100 cc) and saturated sodium chloride solution (100 cc), then dried over magnesium sulphate and treated with a solution of hydrogen chloride gas in isopropyl ether. The oil formed is separated after settling has taken place and crystallized in acetone (30 cc). The crystals are drained, washed with acetone and dried. (3aRS,7aRS)-7,7-Diphenylperhydro-4-isoindolone hydrochloride (0.55 g), m.p. 270° C. with decomposition, is obtained.

4,4-Diphenyl-2-formyl-3-(nitromethyl)cyclohexanone may be prepared in the following manner:

A solution of 4,4-diphenyl-2-formyl-2-cyclohexen-1-one (29 g) and nitromethane (5.7 cc) in a mixture of tetrahydrofuran (250 cc) and tert-butanol (500 cc) is treated with a 35% strength solution (6.93 cc) of benzyltrimethylammonium hydroxide in methanol and stirred at 20° C. for 18 hours. The reaction mixture is diluted with ethyl acetate (500 cc) and water (2000 cc) and acidified to pH 2 with hydrochloric acid. The aqueous phase is extracted with ethyl acetate (200 cc) and the combined organic phases are washed with water (500 cc) and saturated sodium chloride solution (250 cc), then dried over magnesium sulphate and concentrated to dryness under reduced pressure (2.7 kPa). The crystallized residue is stirred in a mixture (100 cc) of cyclohexane and ethyl acetate (80:20 by volume) and the crystals are drained and washed with the same mixture (20 cc) and with isopropyl ether (2×50 cc). 4,4-Diphenyl-2-formyl-3-(nitromethyl)cyclohexanone (24.7 g) is obtained in the form of cream-colored crystals, m.p. 188° C.

4,4-Diphenyl-2-formyl-2-cyclohexen-1-one 4,4-Diphenyl-2-formyl-2-cyclohexen-1-one may be prepared in the following manner:

A solution of 4,4-diphenyl-2-formylcyclohexanone (44.5 g) and 2,3-dichloro-5,6-dicyano-1,4-benzoquinone (38 g) in dioxane (650 cc) is stirred for 30 minutes at 25° C. and then cooled to 0° C.; the solid is removed by filtration and the filtrate is concentrated to dryness under reduced pressure (2.7 kPa). The residue is chromatographed on a column of silica gel (0.2–0.06 mm, diameter 6 cm, height 63 cm), eluting with a mixture of cyclohexane and ethyl acetate (80:20 by volume) and collecting 50-cc fractions. Fractions 7 to 12 are combined and concentrated to dryness under reduced pressure (2.7 kPa). The crystalline residue is stirred vigorously with isopropyl ether (200 cc) and the crystals obtained are drained, washed with isopropyl ether (2×50 cc) and dried. 4,4-Diphenyl-2-formyl-2-cyclohexen-1-one (12 g), m.p. 126° C., is obtained.

4,4-Diphenyl-2-formylcyclohexanone may be prepared in the following manner:

4,4-Diphenylcyclohexanone (40 g) is added to a solution of potassium tert-butylate (66.5 g) in tert-butanol (500 cc), and a solution of ethyl formate (47.6 cc) in tert-butanol (500 cc) is then added dropwise. The reaction mixture is stirred at 50° C. for 8 hours, then cooled and diluted with water (3000 cc) and ethyl acetate (750 cc) and acidified to pH 2 with 4N hydrochloric acid. The aqueous phase is extracted with ethyl acetate (2×250 cc) and the combined organic phases are washed with water (250 cc) and saturated sodium chloride solution (250 cc), then dried over magnesium sulphate and concentrated to dryness under reduced pressure (2.7 kPa). 4,4-Diphenyl-2-formylcyclohexanone (48 g) is obtained, and is used without purification for the next step of the synthesis.

EXAMPLE 17

4N aqueous sodium hydroxide (500 cc) is added slowly and with stirring to a suspension of (3aRS,-

7aRS)-7,7-diphenylperhydro-4-isoindolone hydrochloride (200 g) in ethyl acetate (2000 cc); stirring is continued until the starting material has disappeared. The organic solution is washed with distilled water (250 cc) and with saturated aqueous sodium chloride solution (250 cc), dried over magnesium sulphate and filtered. To the solution thereby obtained, a solution of L(+)-mandelic acid (92.8 g) in ethyl acetate (1000 cc) is added with stirring; after 4 hours' stirring, the crystals obtained are drained, crystals are taken up with distilled water (2000 cc); the mixture is heated to reflux with stirring for 15 minutes; the insoluble crystals are drained, washed with distilled water (2×100 cc) and dried. They are recrystallized in a mixture of acetonitrile (1100 cc) and distilled water (500 cc); the crystals obtained are drained, washed with acetonitrile (3×40 cc) and dried. (3aR,7aR)-7,7-Diphenylperhydro-4-isoindolone L-mandelate (80 g) is obtained; $[\alpha]_D^{20} = -164°$ (c=1, methanol).

1N aqueous sodium hydroxide (400 cc) and ethyl acetate (600 cc) are added to (3aR,7aR)-7,7-diphenylperhydro-4-isoindolone L-mandelate (80 g); the mixture is stirred at room temperature until the starting material has disappeared; the organic solution is washed with distilled water (250 cc) and with saturated aqueous sodium chloride solution (250 cc), dried over magnesium sulphate and filtered; it is acidified, with stirring, by adding 9N hydrochloric acid (30 cc); the crystals obtained are drained, washed with ethyl acetate (2×50 cc) and with isopropyl ether (50 cc) and dried. (3aR,-7aR)-7,7-Diphenylperhydro-4-isoindolone hydrochloride (52.3 g), m.p. 270° C. with decomposition, is obtained; $[\alpha]_D^{20} = -282°$ (c=0.5, methanol).

REFERENCE EXAMPLE 1

N,N'-Carbonyldiimidazole (1.7 g) is added to a solution, cooled to +5° C., of phenylacetic acid (1.34 g) in dry dichloromethane (30 cc). The mixture is stirred for 1 hour at +5° C. and a solution of hydrochloride (3.27 g) and triethylamine (1.7 cc) in dichloromethane (40 cc) is then added. The reaction mixture is stirred for 1 hour at +5° C. and then for 1 hour at 20° C. The reaction hydrogen carbonate solution (50 cc), dried over magnesium sulphate, filtered and concentrated to dryness under reduced pressure (2.7 kPa). The residue is crystallized in acetonitrile (15 cc). The crystals are drained, washed with isopropyl ether (10 cc) and dried. (3aRS,-7aRS)-7,7-Diphenyl-2-(phenylacetyl)perhydro-4-isoindolone (2.7 g), m.p. 216° C., is obtained.

REFERENCE EXAMPLE 2

A solution of phenylacetyl chloride (4 cc) and triethylamine (8.6 cc) in dichloromethane (10 cc) is added dropwise to a solution, cooled to +5° C., of (3aR,7aR)-7,7-diphenylperhydro-4-isoindolone hydrochloride (10 g) in dry dichloromethane (80 cc). The reaction mixture is stirred for 2 hours at +5° C. and then for 20 hours at 20° C. The reaction mixture is treated with saturated aqueous sodium hydrogen carbonate solution (30 cc); the organic phase is washed with distilled water (2×50 cc), dried over magnesium sulphate, filtered and concentrated to dryness under reduced pressure (2.7 kPa). The residue is crystallized in acetonitrile (15 cc). The crystals are drained, washed with acetonitrile (10 cc) and with isopropyl ether (10 cc) and dried. (3aR,7aR)-7,7-Diphenyl-2-(phenylacetyl)perhydro-4-isoindolone (5.7 g), m.p. 173° C. is obtained; $[\alpha]_D^{20} = -282°$ (c=1, methanol).

REFERENCE EXAMPLE 3

Triethyloxonium tetrafuroborate (10.45 g) is added to a solution of (3aRs,7aRS)-7,7-diphenyl-2-phenylacetylperhydro-4-isoindolinone (20 g) in dichloromethane (50 cc). The reaction mixture is left stirring for 20 hours at room temperature. The precipitate obtained is drained, washed with anhydrous dichloromethane (10 cc) and with anhydrous ether (10 cc) and dried; (3aRS,7aRS)-2-(1-ethoxy-2-phenylethylidene)-4-oxo-7,7-diphenylperhydroisondolium tetrafuroborate (11.1 g) is obtained in the form of a white powder, which is used in the crude state for the following manipulations.

A 0.8N solution (8.8 cc) of ammonia in dichloromethane is added to a stirred suspension, cooled to −20° C., of (3aRS,7aRS)-2-(1-ethoxy-2-phenylethylidene)-4-oxo-7,7-diphenylperhydroisoindolium tetrafluoroborate (3.75 g) in anhydrous dichloromethane (30 cc). The reaction mixture is allowed to return to room temperature and stirring is continued for 5 hours. The reaction mixture is treated with 10% strength aqueous potassium carbonate solution (30 cc). The precipitate present is removed by filtration and the organic phase is then washed with distilled water (15 cc) and with saturated aqueous sodium chloride solution (15 cc), dried over magnesium sulphate and concentrated to dryness under reduced pressure (2.7 kPa). The residue is recrystallized in acetonitrile (22 cc). The crystals obtained are drained and dried. (3aRS,7aRS)-2-(α-Iminophenethyl)-7,7-diphenylperhydro-4-isoindolone (1.3 g), m.p. 202° C., is obtained.

REFERENCE EXAMPLE 4

Working in a manner similar to Reference Example 3, starting with the product obtained in Reference Example 2, the following products are prepared:
(3aRS,7aRS)-2-(α-benzyliminophenethyl)-7,7-diphenylperhydro-4-isoindolone, m.p. 165° C.
(3aRS,7aRS)-2-[α-(2-fluorobenzyl)iminophenethyl]-7,7-diphenylperhydro-4-isoindolone, m.p. 160° C.
(3aRS,7aRS)-7,7-diphenyl-2-[α-(2-thienylmethyl)iminophenethyl]perhydro-4-isoindolone, m.p. 114° C.
(3aRS,7aRS)-7,7-diphenyl-2-[α-(2-pyridylmethyl)iminophenethyl]perhydro-4-isoindolone, m.p. 180° C.

REFERENCE EXAMPLE 5

N,N'-Carbonyldiimidazole (1.14 g) is added to a solution, cooled to +5° C., of 2-hydroxyphenylacetic acid (1.06 g) in dry dichloromethane (30 cc). The mixture is stirred for 30 minutes at +5° C. and a solution of (3aRS,7aRS)-7,7-diphenylperhydro-4-isoindolone hydrochloride (2.23 g) and triethylamine (1.96 cc) in dichloromethane (20 cc) is then added. The reaction mixture is stirred at 20° C. for 16 hours, then washed with water (2×100 cc), dried over magnesium sulphate, filtered and concentrated to dryness under reduced pressure (2.7 kPa). The residue is chromatographed on a column of silica gel (0.2–0.063 mm, diameter 4 cm, height 40 cm), eluting under a nitrogen pressure of 0.7 bar with a mixture of cyclohexane and ethyl acetate (70:30 by volume) and collecting 125-cc fractions. Fractions 4 to 11 are combined and concentrated to dryness under reduced pressure (2.7 kPa). The residue is crystallized in a mixture of acetonitrile (15 cc) and isopropyl ether (30 cc). The crystals are drained, washed with isopropyl ether and dried. (3aRS,7aRS)-7,7-Diphenyl- 2-[(2-hydroxyphenyl)acetyl]perhydro-4-isoindolone (0.8 g) is obtained in the form of white crystals, m.p. 232° C.

REFERENCE EXAMPLE 6

N,N'-Carbonyldiimidazole (1.13 g) is added to a solution, cooled to +5° C., of 2-methoxyphenylacetic acid (1.16 g) in dry dichloromethane (30 cc). The mixture is stirred for 15 minutes at +5° C. and a solution of (3aRS,7aRS)-7,7-diphenylperhydro-4-isoindolone hydrochloride (2.28 g) and triethylamine (1.96 cc) in dichloromethane (20 cc) is then added. The reaction mixture is stirred at 20° C. for 16 hours, then washed with water (2×150 cc), dried over magnesium sulphate, filtered and concentrated to dryness under reduced pressure (2.7 kPa). The meringue-like product obtained is crystallized in a mixture of acetonitrile (30 cc) and isopropyl ether (30 cc). The crystals are drained, washed with isopropyl ether (25 cc) and dried. (3aRS,7aRS)-7,7-Diphenyl-2-[(2-methoxyphenyl)acetyl]perhydro-4-isoindolone (2 g) is obtained in the form of white crystals, m.p. 163° C.

REFERENCE EXAMPLE 7

Triethyloxonium tetrafluoroborate (2.35 g) is added to a solution of (3aRS,7aRS)-7,7-diphenyl-2-[(2-methoxyphenyl)acetyl]perhydro-4-isoindolone (5 g) in dichloromethane (10 cc). The reaction mixture is left stirring for 20 hours at room temperature; it is then treated with ether (100 cc) and the precipitate obtained is drained, washed with ether (100 cc) and dried. (3aRS,7aRS)-2-[1-Ethoxy-2-(2-methoxyphenyl)ethylidene]-4-oxo-7,7-diphenylperhydroisoindolium tetrafluoroborate (5.75 g) is obtained in the form of a yellow powder, which is used in the crude state for the following manipulation.

A 5.4N ethanolic solution (1.3 cc) of ammonia is added to a stirred suspension, cooled to −10° C., of (3aRS,7aRS)-2-[1-ethoxy-2-(2-methoxyphenyl)ethylidene]-4-oxo-7,7-diphenylperhydroisoindolium tetrafluoroborate (5.7 g) in anhydrous dichloromethane (15 cc). The reaction mixture is then allowed to return to room temperature and stirring is continued for 20 hours. The reaction mixture is diluted with dichloromethane (20 cc) and treated with 10% strength aqueous potassium carbonate solution (20 cc). The precipitate present is removed by filtration and the organic phase is then washed with distilled water (25 cc) and with saturated aqueous sodium chloride solution (25 cc), dried over magnesium sulphate and concentrated to dryness under reduced pressure (2.7 kPa). The residue is crystallized in acetonitrile (10 cc). The crystals obtained are drained, washed with acetonitrile (10 cc) and dried. and dried. (3aRS,7aRS)-2-[1-Imino-2-(2-methoxyphenyl)ethyl]-7,7-diphenylperhydro-4-isoindolone (1 g), m.p. above 260° C. is obtained.

REFERENCE EXAMPLE 8

N,N'-Carbonyldiimidazole (1 g) is added to a solution, cooled to +5° C., of 2-methoxyphenylacetic acid (1 g) in dry dichloromethane (30 cc). The mixture is stirred for 40 minutes at +5° C. and a solution of (3aR,7aR)-7,7-diphenylperhydro-4-isoindolone hydrochloride (2 g) and triethylamine (1.7 cc) in dichloromethane (40 cc) is then added. The reaction mixture is stirred at 20° C. for 16 hours, then washed with water (2×50 cc), dried over magnesium sulphate, filtered and concentrated to dryness under reduced pressure (2.7 kPa). The residue is chromatographed on a column of silica gel (0.2–0.063 mm, diameter 1.8 cm, height 13 cm), eluting with ethyl acetate and collecting 25-cc fractions. Fractions 3 to 5 are combined and concentrated to dryness under reduced pressure (2.7 kPa). The residue is crystallized in a mixture of acetonitrile (5 cc) and isopropyl ether (10 cc). The crystals are drained, washed with isopropyl ether (25 cc) and dried. (3aR,7aR)-(−)-7,7-Diphenyl-2-[(2-methoxyphenyl)acetyl]perhydro-4-isoindolone (1.7 g) is obtained in the form of white crystals, m.p. 200° C.; $[\alpha]_D^{20} = -274°$ (c=0.49, acetic acid).

REFERENCE EXAMPLE 9

Triethyloxonium tetrafluoroborate (4 g) is added to a solution of (3aR,7aR)-7,7-diphenyl-2-[(2-methoxyphenyl)acetyl]perhydro-4-isoindolone (7.7 g) in anhydrous dichloromethane (13 cc). The reaction mixture is left stirring for 20 hours at room temperature; the mixture is then cooled to −15° C. and thereafter a 5.4N ethanolic solution (2.6 cc) of ammonia is added. The reaction mixture is allowed to return to room temperature and stirring is continued for 5 hours and a half. The reaction mixture is treated with 10% strength aqueous potassium carbonate solution (20 cc); the precipitate formed is drained and washed with dichloromethane (10 cc). The organic phases are combined, dried over magnesium sulphate and concentrated to dryness under reduced pressure (2.7 kPa). The residue is crystallized in acetonitrile (10 cc); the crystals obtained are drained, washed with acetonitrile (5 cc) and with isopropyl ether (10 cc) and dried. They are then chromatographed on a column of Péchiney CBT1 neutral alumina gel (diameter 4.5 cm, height 28 cm), eluting with a mixture (200 cc) of 1,2-dichloroethane and methanol (98:2 by volume) and then with a mixture of 1,2-dichloroethane and methanol (90:10 by volume) and collecting 25-cc fractions. Fractions 8 to 31 are combined and concentrated to dryness under reduced pressure (2.7 kPa). The residue is crystallized in acetonitrile (10 cc); the crystals obtained are drained and dried. (3aR,7aR)-2-[1-Imino-2-(2-methoxyphenyl)ethyl]-7,7-diphenylperhydro-4-isoindolone (1.6 g), m.p. 190° C., is obtained; $[\alpha]_D^{20} = -254°$ (c=1, methanol).

REFERENCE EXAMPLE 10

N,N'-Carbonyldiimidazole (1.62 g) is added to a solution, cooled to +5° C., of (2-tert-butoxycarbonylaminophenyl)acetic acid (2.51 g) in dry dichloromethane (30 cc). The mixture is stirred for 45 minutes at +5° C. and a solution of (3aRS,7aRS)-7,7-diphenylperhydro-4-isoindolone hydrochloride (3.27 g) and triethylamine (2.8 cc) in dichloromethane (30 cc) is then added. The reaction mixture is stirred at 20° C. for 16 hours, then washed with water (3×100 cc), dried over magnesium sulphate, filtered and concentrated to dryness under reduced pressure (2.7 kPa). The residue is chromatographed on a column of silica gel (0.2–0.063 mm, diameter 4 cm, height 40 cm), eluting under a nitrogen pressure of 0.7 bar with a mixture of cyclohexane and ethyl acetate (60:40 by volume) and collecting 125-cc fractions. Fractions 22 to 34 are combined and concentrated to dryness under reduced pressure (2.7 kPa) to give (3aRS,7aRS)-2-[(2-tert-butoxycarbonylaminophenyl)acetyl]-7,7-diphenylperhydro-4-isoindolone (1.5 g) in the form of a yellow meringue-like product.

(3aRS,7aRS)-2-[(2-tert-Butoxycarbonylaminophenyl)acetyl]-7,7-diphenylperhydro-4-isoindolone (1.5 g) is treated with a 5.7N solution (15 cc) of hydrochloric acid in dry dioxane at 20° C. for 4 hours. The reaction mixture is concentrated to dryness under reduced pressure (2.7 kPa) and the residue purified by dissolution in acetonitrile (20 cc) and precipitation with isopropyl ether (30 cc). The solid is drained, washed with isopropyl ether and dried. (3aRS,7aRS)-2-[(2-Aminophenyl)acetyl]-7,7-diphenylperhydro-4-isoindolone hydrochloride (1.1 g) is obtained in the form of a slightly pinkish solid.

Proton NMR spectrum: At room temperature, a mixture of the two rotamers is observed.

2.1 and 2.27 (2 Mt, 1H each, respectively, —CH₂— at position 5 or 6); 2.65 to 3.35 (Mt, 4H, —CH₂— at position 6 or 5 and —CH₂— at position 1); 3.4 to 3.75 (Mt, 1H of the —CH₂— at position 3 and

at position 3a); 3.55 and 3.84

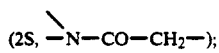

3.9 to 4.2 (Mt, —CH— at position 7a); 4.15 to 4.4 (Mt, 1H of the —CH₂— at position 3); 7 to 7.7 (Mt, 14H, aromatic).

Infrared spectrum (Kbr), characteristic bands (cm⁻¹): 3430, 3085, 3000–1900, 3055, 3025, 2965, 2880, 1715, 1630–1520, 1625, 1595, 1580, 1492, 1455, 755, 703

(2-tert-Butoxycarbonylaminophenyl)acetic acid may be obtained in the following manner:

A solution of (2-nitrophenyl)acetic acid (18.1 g) in normal sodium hydroxide solution (120 cc) is hydrogenated in an autoclave under a pressure of 5 bars in the course of 2.5 hours at 20° C. in the presence of palladinized carbon black (3% palladium) (1.5 g). The solution of the sodium salt of (2-aminophenyl)acetic acid thereby obtained is cooled to +5° C. and then treated with a solution of di-tert-butyl dicarbonate (26.16 g) in tetrahydrofuran (100 cc) and then with normal sodium hydroxide solution (80 cc). The reaction mixture is stirred at 20° C. for 18 hours, partially concentrated under reduced pressure (2.7 kPa), diluted with water (200 cc) and washed with ethyl ether (3×200 cc). The aqueous phase is acidified to pH 3 by adding 4N hydrochloric acid and extracted with ethyl acetate (2×200 cc). The combined organic phases are washed with water (2×150 cc), dried over magnesium sulphate, filtered and concentrated to dryness under reduced pressure (2.7 kPa). (2-tert-Butoxycarbonylaminophenyl)acetic acid (25 g) is obtained in the form of a cream-white solid.

REFERENCE EXAMPLE 11

N,N'-carbonyldiimidazole (1.13 g) is added to a solution, cooled to +5° C., of [2-(N-tert-butoxycarbonyl-N-methylamino)phenyl]acetic acid (1.85 g) in dry dichloromethane (30 cc). The mixture is stirred for 30 minutes at +5° C. and a solution of (3aRS,7aRS)-7,7-diphenylperhydro-4-isoindolone hydrochloride (2.29 g) and triethylamine (1.9 cc) in dichloromethane (20 cc) is then added. The reaction mixture is stirred at 20° C. for 2 hours, then washed with water (2×200 cc), dried over magnesium sulphate, filtered and concentrated to dryness under reduced pressure (2.7 kPa). The residue is chromatographed on a column of silica gel (0.2–0.063 mm, diameter 4 cm, height 50 cm), eluting under a nitrogen pressure of 0.7 bar with a mixture of cyclohexane and ethyl acetate (30:70 by volume) and collecting 125-cc fractions. Fractions 22 to 34 are combined and concentrated to dryness under reduced pressure (2.7 kPa) to give (3aRS,7aRS)-2-{[2-(N-tert-butoxycarbonyl-N-methylamino)phenyl]acetyl}-7,7-diphenylperhydro-4-isoindolone (2.8 g) in the form of a white meringue-like product.

(3aRS,7aRS)-2-{[2-(N-tert-Butoxycarbonyl-N-methylamino)phenyl]acetyl}-7,7-diphenylperhydro-4-isoindolone (2.8 g) is treated with a 5.7N solution (30 cc) of hydrochloric acid in dry dioxane at 20° C. for 4 hours. Isopropyl ether (100 cc) is added and the solid is drained, washed with isopropyl ether and dried. (3aRS,7aRS)-2-[(2-methylaminophenyl)acetyl]-7,7-diphenylperhydro-4-isoindolone hydrochloride (2.1 g) is obtained in the form of a white solid.

Proton NMR spectrum: At room temperature, a mixture of the two rotamers is observed.

2.1 to 2.27 (2 Mt, 1H each, respectively, —CH₂— at position 5 or 6); 2.65 to 3.35 (Mt, —CH₂— at position 6 or 5 and —CH₂— at position 1); 2.82 and 2.87

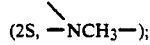

3.4 to 3.75 (Mt, 1H of the —CH₂— at position 3 and

at position 3a); 3.55 and 3.85

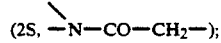

3.9 to 4.2 (Mt,

at position 7a); 4.15 to 4.45 (Mt, 1H of the —CH₂— at position 6 or 5); 7 to 7.7 (Mt, 14H, aromatic).

Infrared spectrum (KBr), characteristic bands (cm⁻¹): 3600–3300, 3100–3000, 3000–2850, 3100–2200, 1712, 1640–1610, 1595, 1495, 1475–1410, 1445, 755, 702.

[2-(N-tert-Butoxycarbonyl-N-methylamino)-phenyl]acetic acid may be prepared in the following manner:

A solution of methyl [2-(N-tert-butoxycarbonyl-N-methylamino)phenyl]acetate (3.5 g) in ethanol (50 cc) is treated with normal sodium hydroxide solution (15 cc) at 80° C. for 4 hours. The reaction mixture is concentrated under reduced pressure (2.7 kPa). The residue is taken up with water (100 cc) and the solution, acidified to pH 1 with 4N hydrochloric acid, is extracted with ethyl acetate (2×100 cc). The combined organic phases are dried over magnesium sulphate, filtered and concentrated to dryness under reduced pressure (2.7 kPa) to give [2-(N-tert-butoxycarbonyl-N-methylamino)phenyl]acetic acid (2.85 g) in the form of a white solid.

Methyl [2-(N-tert-butoxycarbonyl-N-methylamino)-phenyl]acetate may be prepared in the following manner:

A solution of 2-tert-butoxycarbonylaminophenyl)acetic acid (5 g) in dry dimethylformamide (50 cc) is added to a suspension of sodium hydride (80% dispersion in oil) (1.2 g) in dry dimethylformamide (20 cc). The reaction mixture is heated to 80° C. for 2 hours and cooled to 20° C. Methyl iodide (2.51 cc) is added and the mixture is stirred at 20° C. for 16 hours. It is diluted with water (200 cc) and extracted with ethyl acetate (2×200 cc). The combined organic phases are washed with water (100 cc), dried over magnesium sulphate, filtered and concentrated to dryness under reduced pressure (2.7 kPa). The residue is chromatographed on a column of silica gel (0.2–0.063 mm, diameter 4 cm, height 48 cm), eluting under a nitrogen pressure of 0.7 bar with a mixture of cyclohexane and ethyl acetate (90:10 by volume) and collecting 125-cc fractions. Fractions 9 to 17 are combined and concentrated to dryness under reduced pressure (2.7 kPa) to give methyl [2-(N-tert-butoxycarbonyl-N-methylamino)phenyl]acetate (3.5 g) in the form of a yellow oil.

REFERENCE EXAMPLE 12

N,N'-carbonyldiimidazole (1 g) is added to a solution, cooled to +5° C., of 2-dimethylaminophenylacetic acid (1.1 g) in dry dichloromethane (30 cc). The mixture is stirred for 30 minutes at +5° C. and a solution of (3aRS, 7aRS)- 7,7-diphenylperhydro-4-isoindolone hydrochloride (2.03 g) and triethylamine (1.68 cc) in dichloromethane (20 cc) is then added. The reaction mixture is stirred at 20° C. for 24 hours, then washed with water (3×200 cc), dried over magnesium sulphate, filtered and concentrated to dryness under reduced pressure (2.7 kPa). The residue is chromatographed on a column of silica gel (0.2–0.063 mm, diameter 3 cm, height 25 cm), eluting under a nitrogen pressure of 0.7 bar with a mixture of cyclohexane and ethyl acetate (40:60 by volume) and collecting 125-cc fractions. Fractions 8 to 26 are combined and concentrated to dryness under reduced pressure (2.7 kPa). The residue is crystallized in isopropyl ether (40 cc). The crystals are drained, washed with isopropyl ether and dried. (3aRS, 7aRS)-7,7-Diphenyl-2-[2-(2-dimethylaminophenyl)acetyl]perhydro-4-isoindolone (0.9 g) is obtained in the form of white crystals, m.p. 150° C.

2-Dimethylaminophenylacetic acid is prepared according to the method of D-U. Lee, K. K. Mayer and W. Wiegrebe (Arch. Pharm. (Weinheim), 321, 303 (1988)).

REFERENCE EXAMPLE 13

N,N'-carbonyldiimidazole (2.43 g) is added to a solution, cooled to +5° C., of 2-dimethylaminophenylacetic acid (2.68 g) in dry dichloromethane (50 cc). The mixture is stirred for 90 minutes at +5° C. and a solution of (3aR, 7aR)-7,7-diphenylperhydro-4-isoindolone hydrochloride (4.9 g) and triethylamine (4.2 cc) in dichloromethane (50 cc) is then added. The reaction mixture is stirred at 20° C. for 16 hours, then washed with water (2×100 cc), dried over magnesium sulphate, filtered and concentrated to dryness under reduced pressure (2.7 kPa). The residue is chromatographed on a column of silica gel (0.2–0.063 mm, diameter 5 cm, height 50 cm), eluting under a nitrogen pressure of 0.7 bar with a mixture of cyclohexane and ethyl acetate (40:60 by volume) and collecting 125-cc fractions. Fractions 5 to 20 are combined and concentrated to dryness under reduced pressure (2.7 kPa). The residue is crystallized in a mixture of acetonitrile (40 cc) and isopropyl ether (200 cc). The crystals are drained, washed with isopropyl ether and dried. (3aR, 7aR)-7,7-Diphenyl-2-[2(2-dimethylaminophenyl)acetyl]perhydro-4-isoindolone (2.58 g) is obtained in the form of white crystals, m.p. 190° C.; $[\alpha]_D^{20} = -242°$ (c=1.18, chloroform).

REFERENCE EXAMPLE 14

N,N'-carbonyldiimidazole (0.66 g) is added to a solution, cooled to +5° C., of (S)-2-phenylpropionic acid (0.62 g) in dry dichloromethane (30 cc). The mixture is stirred for 40 minutes at +5° C. and a solution of (3aR, 7aR)-7,7-diphenylperhydro-4-isoindolone hydrochloride (1.35 g) and triethylamine (0.57 cc) in dichloromethane (40 cc) is then added. The reaction mixture is stirred at 20° C. for 16hours, then washed with distilled water (2×50 cc), dried over magnesium sulphate, filtered and concentrated to dryness under reduced pressure (2.7 kPa). The residue is chromatographed on a column of silica gel (0.2–0.063 mm, diameter 1.8 cm, height 15 cm), eluting with ethyl acetate and collecting 15-cc fractions. The first fraction is concentrated to dryness under reduced pressure (2.7 kPa). (3aR, 7aR)-7,7-Diphenyl-2-[2(S)-2-phenylpropionyl]perhydro-4-isoindolone (1 g) is obtained in the form of a white meringue-like product; $[\alpha]_D^{20} = -231°$ (c=1, methanol).

Proton NMR spectrum: At room temperature, a mixture of the two rotamers is observed.

1.16 and 1.26 (2D, 3H in total, —CH₃); 1.95 to 2.3 (Mt, 2H, —CH₂— at position 5 or 6); 2.65 to 2.9 (Mt, 4H, —CH₂— at position 6 or 5 and —CH₂— at position 1); 3.05 to 3.35 (Mt, 2H, 1H of the —CH₂— at position 3 and

at position 3a); 3.4 and 3.8 to 4

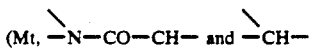

at position 7a); 4.2 to 4.4 (Mt, 1H, 1H of the —CH₂— at position 3); 6.9 to 7.6 (Mt, 15H, aromatic).

Infrared spectrum (KBr), characteristic bands (cm⁻¹): 3600–3300, 3100–3000, 3000–2870, 1715, 1640, 1600, 1580 1495, 1455, 1445, 1420, 1370, 755, 700.

REFERENCE EXAMPLE 15

1H hydroxybenzotriazole (0.59 g) is added to a solution of 84% optically pure (S)-2-(2-methoxyphenyl)propionic acid (0.75 g), prepared according to T. Matsumoto et al., Bull. Chem. Soc. Jpn., 58, 340 (1985) in dry dimethylformamide (15 cc), and the solution is then cooled to 0° C. N,N'-Dicyclohexylcarbodiimide (0.91 g) is then added, the mixture is stirred for 1 hour at this temperature and a solution of (3aR, 7aR)-7,7-diphenyl-perhydro-4-isoindolone hydrochloride (1.44 g) and N,N-diisopropylethylamine (0.76 cc) in dimethylformamide (10 cc) is then added. The reaction mixture is stirred at 20° C. for 16 hours, diluted with ethyl acetate (100 cc) and concentrated to dryness under reduced pressure (2.7 kPa) after the precipitate has been filtered off. The residue is chromatographed on a column of silica gel (0.2–0.063 mm, diameter 3 cm, height 40 cm), eluting under a nitrogen pressure of 0.7 bar with a mixture of cyclohexane and ethyl acetate (50:50 by volume) and collecting 125-cc fractions. Fractions 4 to 7 are combined and concentrated to dryness under reduced pressure (2.7 kPa). The residue is purified by dissolution in boiling isopropyl ether (60 cc) to which hexane (30 cc) is added. The cooled solution is filtered and the filtrate concentrated to dryness under reduced pressure (2.7 kPa) to give (3aR, 7aR)-7,7-diphenyl-2-[(S)-2-(2-methoxyphenyl)propionyl]perhydro-4-isoindolone (1.2 g) in the form of a white meringue-like product containing (3aR, 7aR)-7,7-diphenyl-2-[(R)-2-(2-methoxyphenyl)propionyl]perhydro-4-isoindolone (10%); $[\alpha]_D^{20} = -181°$ (c=0.81, chloroform).

Proton NMR spectrum:

At room temperature, a mixture of the two rotamers of each of the two diastereoisomers is observed; the two diastereoisomers being in the proportions 90:10. 1.10 and 1.20 (2 Mt, 3H in total, —CH$_3$); 1.9 to 2.4 (Mt, 2H, —CH$_2$— at position 5 or 6); 2.55 to 2.95 (Mt, —CH$_2$— at position 1 and —CH$_2$— at position 6 or 5); 2.95 to 3.4 (Mt, 1H of the —CH$_2$— at position 3 and

at position 3a); 3.20, 3.32, 3.50 and 3.83 (4S, —OCH$_3$); 3.65 to 4.3 (Mt,

at position 7a,

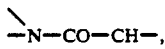

1H of the —CH$_2$— at position 3); 6.7 to 7.65 (Mt, 14H, aromatic).

Infrared spectrum (KBr), characteristic bands (cm$^{-1}$): 3430, 3100–3000, 3000–2800, 1715, 1640, 1595, 1585, 1490, 1460, 1445, 1420, 1365, 1240, 1030, 755, 703.

REFERENCE EXAMPLE 16

N,N′-carbonyldiimidazole (0.85 g) is added to a solution, cooled to 5° C., of (RS)-2-(2-dimethylaminophenyl)propionic acid (1 g) in dichloromethane (30 cc), and the mixture is stirred for 30 minutes at this temperature. A solution of (3aR, 7aR)-7,7-diphenylperhydro-4-isoindolone hydrochloride (1.7 g) and triethylamine (1.4 cc) in dichloromethane (30 cc) is added. The reaction mixture is stirred at 20° C. for 16 hours, washed with water (2×100 cc), dried over magnesium sulphate and concentrated to dryness under reduced pressure (2.7 kPa). The residue is chromatographed on a column of silica gel (0.2–0.063 mm, diameter 3 cm, height 50 cm), eluting under a nitrogen pressure of 0.5 bar with ethyl acetate and collecting 125-cc fractions. Fractions 4 to 6 are combined and concentrated to dryness under reduced pressure (2.7 kPa) to give (3aR, 7aR)-2-[(RS)-2-(2-dimethylaminophenyl)propionyl]-7,7-diphenylperhydro-4-isoindolone (1.4 g) in the form of white meringue-like product;

Proton NMR spectrum: At room temperature, a mixture of the two rotamers of each of the two diastereoisomers is observed. 1.15 to 1.35 (Mt, 3H, —CH$_3$); 1.9 to 2.4 (Mt, —CH$_2$— at position 5 or 6); 2.1, 2.19, 2.62 and 2.64 (4S, —N(CH$_3$)$_2$); 2.55 to 3.4 (Mt, —CH$_2$— at position 6 or 5, —CH$_2$— at position 1, —CH— at position 3a and 1H of the —CH$_2$— at position 3); 3.5 to 4.5 (Mt, —N—CO—CH—, 1H of the —CH$_2$— at position 3 and —CH at position 7a); 7 to 7.7 (Mt, 15H, aromatic).

Infrared spectrum (KBr), characteristic bands (cm$^{-1}$): 3600–3300, 3100–3000, 3000–2780, 1715, 1640, 1595, 1580, 1490, 1460, 1445, 1410, 750, 702.

A solution of 2-(2-dimethylaminophenyl)acetic acid (1.8 g) in dry tetrahydrofuran (10 cc) is added at 10° C. to a solution of lithium diisopropylamide (prepared by the action of a 1.6M solution (2.6 cc) of butyllithium in hexane on a solution of diisopropylamine (2.8 g) in dry tetrahydrofuran (30 cc) at 10° C.). The reaction mixture is stirred for 30 minutes at 20° C. and then for 30 minutes at 35° C. After cooling to 20° C., methyl iodide (0.63 cc) is added and the mixture is heated to 35° C. for 1 hour. It is cooled and diluted with water (20 cc) and ethyl acetate (100 cc). The aqueous phase is washed with ethyl acetate (100 cc), acidified to pH 5 with hydrochloric acid and extracted with ethyl acetate (2×100 cc). The organic phases are washed with water, dried over magnesium sulphate and concentrated to dryness under reduced pressure (2.7 kPa) to give (RS)-2-(2-dimethylaminophenyl)propionic acid (1 g) in the form of a yellow oil.

REFERENCE EXAMPLE 17

Phenylacetyl chloride (0.82 cc) is added to a solution, cooled to +5° C., of 7,7-diphenyl-2,3,3a,4,7,7a-hexahydro-1H-isoindol-4-one hydrochloride (2 g) and triethylamine (1.7 cc) in dry dichloromethane (20 cc). The reaction mixture is stirred for 1 hour at +5° C. and for 1 hour at room temperature; it is washed with distilled water (2×20 cc), dried over magnesium sulphate, filtered and concentrated to dryness under reduced pressure (2.7 kPa). The residue is crystallized in acetonitrile (15 cc). The crystals are drained, washed with isopropyl ether (10 cc), dried and then recrystallized in acetonitrile (20 cc). The crystals obtained are drained and dried. (3aRS, 7aRS)-7,7a-Diphenyl-2-(phenylacetyl)-2,3,3a,4,7,7a-hexahydro-1H-isoindol-4-one (2.7 g), m.p. 188° C., is obtained.

REFERENCE EXAMPLE 18

A suspension, cooled to +4°·C., of 7,7-bis(3-fluorophenyl)perhydro-4-isoindolone hydrochloride (1.5 g) in dichloromethane (30 cc) is treated with triethylamine (1.15 cc) and then with phenylacetyl chloride (0.63 g). The reaction mixture is stirred for 5 hours at 25° C. and then washed with water (3×100 cc). The organic phase is dried over magnesium sulphate, filtered and concentrated to dryness under reduced pressure (2.7 kPa). The residue is chromatographed on a column of silica gel (particle size 0.04–0.063 mm, diameter 2.3 cm, height 25 cm), eluting under a nitrogen pressure of 0.5 bar with a mixture of cyclohexane and ethyl acetate (55:45 by volume), to give a meringue-like product (1.21 g) which is crystallized by adding isopropyl ether (10 cc). The crystals are drained, washed with isopropyl ether and dried. (3aRS, 7aRS)-7,7-Bis(3-fluorophenyl)-2-(phenylacetyl)perhydro-4-isoindolone (0.76 g) is obtained. M.p. 108° C.

REFERENCE EXAMPLE 19

A solution of (2-methoxyphenyl)acetic acid (0.46 g) in dry dichloromethane (15 cc) is cooled to 0° C., then treated with N,N'-carbonyldiimidazole (0.45 g) and stirred for 1 hour at 0° C. A solution of 7,7-bis(3-fluorophenyl)perhydro-4-isoindolone hydrochloride (1 g) and triethylamine (0.76 cc) in dichloromethane (20 cc) is added dropwise. The reaction mixture is stirred for 3 hours at 25° C. and then washed with water (2×50 cc) and with saturated sodium chloride solution (50 cc). The organic phase is dried over magnesium sulphate, filtered and concentrated to dryness under reduced pressure (2.7 kPa). The residue is chromatographed on a column of silica gel (particle size 0.04–0.063 mm, diameter 2.2 cm, height 23 cm), eluting under a nitrogen pressure of 0.5 bar with a mixture of cyclohexane and ethyl acetate (70:30 by volume) and collecting 15-cc fractions. Fractions 4 to 9 are combined and concentrated to dryness under reduced pressure (2.7 kPa), and the product obtained is recrystallized in acetonitrile. The crystals are drained, washed with isopropyl ether and dried. (3aRS,7aRS)-7,7-Bis(3-fluorophenyl)-2-(phenylacetyl)perhydro-4-isoindolone (0.76 g) is obtained. M.p. 194° C.

REFERENCE EXAMPLE 20

A suspension of (2-methoxyphenyl)acetamide (0.9 g) in dry dichloromethane (3 cc) is treated with triethyloxonium tetrafluoroborate (1.14 g), and the solution obtained stirred for 20 hours at 25° C. After cooling to 0° C., a solution of 7,7-bis(3-fluorophenyl)perhydro-4-isoindolone hydrochloride (1.5 g) and triethylamine (1.4 cc) in dichloromethane (9 cc) is added to the reaction medium. The reaction mixture is stirred for 30 minutes at 25° C., then heated to reflux for 5 hours and finally stirred for a further 16 hours at 25° C. Saturated potassium carbonate solution (50 cc) is added, the mixture is stirred and filtered and the organic phase is washed with water (2×50 cc). After drying over magnesium sulphate, filtration and concentration to dryness under reduced pressure (2.7 kPa), the residue is chromatographed on a column of alumina (diameter 2.6 cm, height 24 cm), eluting under a nitrogen pressure of 0.5 bar with a mixture of 1,2-dichloroethane and methanol (95:5 by volume) and collecting 15-cc fractions. Fractions 7 to 25 are combined and concentrated to dryness under reduced pressure (2.7 kPa) to give (3aRS,7aRS)-7,7-bis(3-fluorophenyl)-2-[1-imino-2-(2-methoxyphenyl)ethyl]perhydro-4-isoindolone (0.54 g) in the form of a pale yellow meringue-like product.

Proton NMR spectrum (CDCl$_3$): 2.20 and 2.45 (2m, 2H, —CH$_2$— at position 5); 2.8 (m, 2H, —CH$_2$— at position 6); 3.08 (m, 2H, —CH$_2$— at position 1); 3.23 (m, 1H, H at position 3a); 3.53 (dd, J=11 and 6.5, 1H, 1H of the —CH$_2$— at position 3); 3.6 (s, 2H, —CH$_2$—Ar); 3.8 (m, 1H, H at position 7a); 3.8 (s, 3H, OCH$_3$); 4.43 (d, J=11, 1H, 1H of the —CH$_2$— at position 3); 6.8 to 7.5 (m, 14H aromatic).

Infrared spectrum (characteristic bands in cm$^{-1}$): 3425, 3100–3000, 300–2850, 2835, 1715, 1592, 1610, 1595, 1460, 1250, 1030, 780, 755, 695.

REFERENCE EXAMPLE 21

N,N'-Carbonyldiimidazole (0.59 g) is added to a solution, cooled to +4° C., of (2-dimethylaminophenyl)acetic acid (0.65 g) in dry dichloromethane (20 cc). The mixture is stirred for 90 minutes at 25° C. and a solution of 7,7-bis(3-fluorophenyl)perhydro-4-isoindolone hydrochloride (1.3 g) and triethylamine (1.02 cc) in dry dichloromethane (25 cc) is then added dropwise. The reaction mixture is stirred for 16 hours at 25° C. and washed with water (2×250 cc) and with saturated sodium chloride solution (250 cc). The organic phase is dried over magnesium sulphate and concentrated to dryness under reduced pressure (2.7 kPa). The residue is chromatographed on a column of silica gel (particle size 0.04–0.063 mm, diameter 2.3 cm, height 23 cm), eluting under a nitrogen pressure of 0.5 bar with a mixture of cyclohexane and ethyl acetate (55:45) and collecting 15-cc fractions. Fractions 6 to 18 are combined and concentrated to dryness under reduced pressure (2.7 kPa). The residue is solidified with isopropyl ether to give (3aRS,7aRS)-7,7-bis(3-fluorophenyl)-2-[(2-dimethylaminophenyl)acetyl]perhydro-4-isoindolone (0.6 g), the hydrochloride of which is prepared by dissolution in ethyl acetate (1 cc) and the addition of a 3N solution of hydrochloric acid in isopropyl ether. The precipitate is drained, washed with isopropyl ether and dried. (3aRS,7aRS)-7,7-Bis(3-fluorophenyl)-2-[(2-dimethylaminophenyl)acetyl]perhydro-4-isoindolone hydrochloride (0.48 g) is obtained in the form of a white solid.

Proton NMR spectrum (DMSO-d$_6$/AcOD 90:10): At room temperature, a mixture of the two rotamers is observed. 2 to 2.32 (m, 2H, —CH$_2$— at position 5); 2.37 and 2.6 (2s, 3H each, —N(CH$_3$)$_2$); 2.65 to 3 (m, 4H, —CH$_2$— at position 6 and —CH$_2$— at position 1); 3.15 to 3.3 (m, 1H, H at position 3a); 3.35 and 3.47 (2m, 1H, 1H at position 3); 3.35 and 3.5 (2d, J=15, ArCH$_2$CO of one rotamer); 3.67 (s, ArCH$_2$CO of the other rotamer); 4 (m, 1H, H at position 7a); 4.2 and 4.25 (2m, J=11, 1H, 1H at position 3); 6.9 to 7.6 (m, 12H, aromatic).

Infrared spectrum (characteristic bands in cm$^{-1}$): 3500–3150, 3100–3000, 3000–2850, 1712, 1650, 1615, 1595, 1580, 1495, 1445, 1535, 755, 700.

REFERENCE EXAMPLE 22

N,N'-Carbonyldiimidazole (0.44 g) is added to a solution, cooled to +4° C., of (2-dimethylaminophenyl)acetic acid (0.49 g) in dry dichloromethane (20 cc). The mixture is stirred for 1 hour at 25° C. and a solution of 7,7-bis(2-fluorophenyl)perhydro-4-isoindolone hydrochloride (1 g) and triethylamine (0.76 cc) in dry dichloromethane (25 cc) is then added dropwise. The reaction mixture is stirred for 20 hours at 25° C. and washed with water (2×100 cc) and with saturated sodium chloride solution (100 cc). The organic phase is dried over magnesium sulphate and concentrated to dryness under reduced pressure (2.7 kPa). The residue is chromatographed on a column of silica gel (particle size 0.04–0.063 mm, diameter 2 cm, height 23 cm), eluting under a nitrogen pressure of 0.5 bar with a mixture of cyclohexane and ethyl acetate (50:50) and collecting 10-cc fractions. Fractions 14 to 36 are combined and concentrated to dryness under reduced pressure (2.7 kPa) to give (3aRS,7aRS)-7,7-bis(2-fluorophenyl)-2-[(2-dimethylaminophenyl)acetyl]perhydro-4-isoindolone (1 g), the hydrochloride of which is prepared by dissolution in ethyl acetate (2 cc) and the addition of a 3N solution of hydrochloric acid in isopropyl ether. The precipitate is drained, washed with isopropyl ether and dried. (3aRS,7aRS)-7,7-Bis(2-fluorophenyl)-2-[(2-dimethylaminophenyl)acetyl]perhydro-4-isoindolone hydrochloride (0.87 g) is obtained in the form of a white solid.

Proton NMR spectrum (DMSO-d$_6$/AcOD 90:10); at room temperature, a mixture of the two rotamers is observed: 2.1 to 2.35 (m, 2H, —CH₂— at position 5); 2.8 to 3.4 (m, 10H, —CH₂— at positions 1 and 6, N(CH₃)₂); 3.7 and 3.5 (2 broad dd, 1H, H at position 3a); 3.8 (broad dd, 1H, 1H at position 3); 4.05 (broad s, 2H, —CH₂CO); 4.1 (broad m, 1H, H at position 7a); 4.2 and 4.45 (d, 1H, 1H at position 3); 7 to 8 (m, 12H aromatic).

REFERENCE EXAMPLE 23

Triethylamine (0.45 cc) and then phenylacetyl chloride (0.49 g) are added to a solution, cooled to +4° C., of 7,7-bis(3-chlorophenyl)perhydro-4-isoindolone hydrochloride (1.06 g) in dichloromethane (20 cc). The reaction mixture is stirred for 2 hours at 25° C. and then washed with water (3×30 cc) and saturated sodium chloride solution (3×30 cc). The organic phase is dried over magnesium sulphate, filtered and concentrated to dryness under reduced pressure (2.7 kPa). The residue is chromatographed on a column of silica gel (particle size 0.04–0.063 mm, diameter 2.2 cm, height 23 cm), eluting under a nitrogen pressure of 0.5 bar with a mixture of cyclohexane and ethyl acetate (55:45) and collecting 15-cc fractions. Fractions 7 to 18 are concentrated to dryness under reduced pressure (2.7 kPa) and the residue is crystallized in acetonitrile. The crystals are drained, washed with isopropyl ether and dried. (3aRS,7aRS)-7,7-Bis(3-chlorophenyl)-2-(phenylacetyl)perhydro-4-isoindolone (0.21 g) is obtained. M.p. 160° C.

REFERENCE EXAMPLE 24

A suspension, cooled to +4° C., of (3aRS,7aRS)-7,7-bis(3-tolyl)perhydro-4-isoindolone hydrochloride (1.5 g) in dichloromethane (30 cc) is treated with triethylamine (1.15 cc) and then with phenylacetyl chloride (0.63 g). The reaction mixture is stirred for 5 hours at 25° C. and then washed with water (3×100 cc). The organic phase is dried over magnesium sulphate, filtered and concentrated to dryness under reduced pressure (2.7 kPa). The residue is crystallized twice in acetonitrile to give (3aRS,7aRS)-7,7-bis(30tolyl)-2-(phenylacetyl)perhydro-4-isoindolone (0.36 g). M.p. 207° C.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A isoindolone derivative of formula:

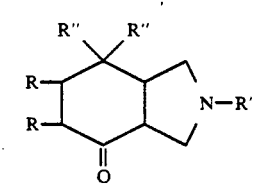

in which the radicals R represent hydrogen atoms or, together, form a bond, the symbol R' represents a hydrogen atom or an allyl radical or a radical of structure:

in which $R_a$ and $R_b$ are hydrogen atoms or phenyl radicals, optionally substituted, with a halogen atom or an alkyl, alkyloxy or nitro radical, and $R_c$ is defined as $R_a$ and $R_b$ or represents an alkyl or alkyloxyalkyl radical, at least one $R_a$, $R_b$ and $R_c$ being a substituted or unsubstituted phenyl radical, and the symbols R" are identical and represent phenyl radicals which can be substituted with a halogen atom or a methyl radical at the ortho or meta position, in the (3aR,7aR) form or in the form of a mixture of the (3aRS,7aRS) forms, or an acid addition salt.

2. A isoindolone derivative according to claim 1, wherein the alkyl radicals and portions mentioned above are linear or branched and contain 1 to 4 carbon atoms.

3. A isoindolone derivative according to claim 1, wherein the radicals R are hydrogen atoms or, together, form a bond, the symbol R' is a hydrogen atom or a benzyl radical and the symbols R" are phenyl radicals optionally substituted at the ortho or meta position with fluorine or chlorine atoms or with a methyl radical.

4. 7,7-Diphenylperhydro-4-isoindolone in its (3aR,7aR) or (3aRS,7aRS) forms, or an acid addition salt.

5. 7,7-Bis(3-fluorophenyl)perhydro-4-isoindolone in its (3aR,7aR) or (3aRS,7aRS) forms, or an acid addition salt.

6. 7,7-Bis(2-fluorophenyl)perhydro-4-isoindolone in its (3aR,7aR) or (3aRS,7aRS) forms, or an acid addition salt.

7. 7,7-Bis(3-chlorophenyl)perhydro-4-isoindolone in its (3aR,7aR) or (3aRS,7aRS) forms, or an acid addition salt.

8. 7,7-Bis(3-tolyl)perhydro-4-isoindolone in its (3aR,7aR) or (3aRS,7aRS) forms, or an acid addition salt.

* * * * *